(12) United States Patent
Roepman et al.

(10) Patent No.: US 8,921,051 B2
(45) Date of Patent: Dec. 30, 2014

(54) METHODS AND MEANS FOR TYPING A SAMPLE COMPRISING COLORECTAL CANCER CELLS

(75) Inventors: Paul Roepman, Utrecht (NL); Annuska Maria Glas, Assendelft (NL)

(73) Assignee: Agendia B.V., Amsterdam (NL)

( * ) Notice: Subject to any disclaimer, the term of this patent is extended or adjusted under 35 U.S.C. 154(b) by 202 days.

(21) Appl. No.: 13/141,742

(22) PCT Filed: Dec. 23, 2009

(86) PCT No.: PCT/NL2009/050797
§ 371 (c)(1),
(2), (4) Date: Sep. 6, 2011

(87) PCT Pub. No.: WO2010/074573
PCT Pub. Date: Jul. 1, 2010

(65) Prior Publication Data
US 2011/0319285 A1 Dec. 29, 2011

(30) Foreign Application Priority Data

Dec. 24, 2008 (EP) ..................... 08172911

(51) Int. Cl.
*C12Q 1/68* (2006.01)
*G01N 33/53* (2006.01)

(52) U.S. Cl.
CPC ........ *C12Q 1/6886* (2013.01); *C12Q 2600/118* (2013.01); *C12Q 2600/158* (2013.01); *C12Q 2600/106* (2013.01); *C12Q 2600/136* (2013.01); *C12Q 2600/112* (2013.01)
USPC .................. 435/6.14; 435/7.1; 506/9; 506/16

(58) Field of Classification Search
None
See application file for complete search history.

(56) References Cited

U.S. PATENT DOCUMENTS

| 6,204,375 B1 | 3/2001 | Lader |
| 7,138,226 B2 | 11/2006 | Vincek et al. |
| 2005/0130170 A1 | 6/2005 | Harvey et al. |

FOREIGN PATENT DOCUMENTS

| DE | 10021390.1 A1 | 5/2000 |
| WO | 98/20355 A1 | 5/1998 |
| WO | 02103320 A2 | 12/2002 |
| WO | 03068788 A1 | 8/2003 |
| WO | 2004083369 A2 | 9/2004 |

OTHER PUBLICATIONS

Strausberg & Klausner, in Microarrays and Cancer Research, 2002, Warrington et al (eds.), Eaton Publishing, Westborough, MA, pp. xi-xvi at p. xi, last full paragraph.*

Notterman et al, in Microarrays and Cancer Research, 2002, Warrington et al (eds.), Eaton Publishing, Westborough, MA, pp. 81-111 at pp. 81-82.*
Ries, et al.—SEER Cancer Statistics Review 1975-2003—National Cancer Institute, Bethesda, MD. 2006—May 3, 2006.
Alberto Sobrero—Should adjuvant chemotherapy become standard treatment for patients with stage II colon cancer?—Department of Medical Oncology, Ospedale San Martino, Genoa, 16132, Italy—The Lancet Oncology—Jun. 2006, vol. 7, pp. 515-517.
Thierry Andre, MD., et al.—Current Issues in Adjuvant Treatment of Stage II Colon Cancer—Annals of Surgical Oncology—vol. 13(6), pp. 887-898—Published by Springer Science & Business Media, Inc. © 2006 The Society of Surgical Oncology, Inc.
Al B. Benson, III, et al.,—American Society of Clinical Oncology Recommendations on Adjuvant Chemotherapy for Stage II Colon Cancer—Journal of Clinical Oncology—vol. 22, No. 16, Aug. 15, 2004, pp. 3408-3419—© 2004 American Society of Clinical Oncology.
E.J.D. Van Cutsem, et al.—ESMO Minimum Clinical Recommendations for diagnosis, treatment and follow-up of advanced colorectal cancer—Annals of Oncology—16 (Supplement 1); pp. i18-i19, 2005—© 2005 European Society for Medical Oncology.
Sharlene Gill, et al.—Pooled Analysis of Fluorouracil-Based Adjuvant Therapy for Stage II and III Colon Cancer: Who Benefits and by How Much?—Journal of Clinical Oncology—vol. 22, No. 10, May 15, 2004, pp. 1797-1806—© 2004 American Society of Clinical Oncology.
T.E. Le Voyer, et al., Colon Cancer Survival Is Associated With Increasing Number of Lymph Nodes Analyzed: A Secondary Survey of Intergroup Trial INT-0089—Journal of Clinical Oncology—vol. 21, No. 15 (Aug. 1), 2003, pp. 2912-2919—© 2003 by American Society of Clinical Oncology.
Richard M. Simon, et al.—Design and Analysis of DNA Microarray Investigations—Statistics for Biology and Health—Springer-Verlag New York Berlin Heidelberg—2003.
Edward L. Korn, et al.—Controlling the number of false discoveries: application to high-dimensional genomic data—Journal of Statistical Planning and Inference—124 (2004) pp. 379-398.
Shung-Haur Yang, et al.—Potential of faecal RNA in diagnosing colorectal cancer—Cancer Letters—226 (2005), pp. 55-63.
Eric Eldering, et al.—Expression profiling via novel multiplex assay allows rapid assessment of gene regulation in defined signalling pathways—Nucleic Acids Research, 2003, vol. 31, No. 23 e153—© Oxford University Press 2003.
Marie-Laure Martin-Magniette, et al.—Evaluation of the gene-specific dye bias in cDNA microarray experiments—Bioinformatics—vol. 21, No. 9 (2005), pp. 1995-2000—Published by Oxford University Press 2005.
Yee Hwa Yang, et al.—Normalization for cDNA microarray data: a robust composite method addressing single and multiple slide systematic variation—Nucleic Acids Research, 2002, vol. 30, No. 4 e15—© 2002 Oxford University Press.

(Continued)

*Primary Examiner* — Catherine Hibbert
(74) *Attorney, Agent, or Firm* — Hoffmann & Baron, LLP

(57) ABSTRACT

The invention relates to a method of typing colorectal cancer cells by determining the RNA levels of a set of signature genes. Said typing can be use for predicting a risk for recurrence of said colorectal cancer. The invention further relates to a set of genes that can be used for normalizing the RNA levels of said set of signature genes, and to micro-array comprising said set of signature genes.

12 Claims, 9 Drawing Sheets

(56) References Cited

OTHER PUBLICATIONS

Figure 1:
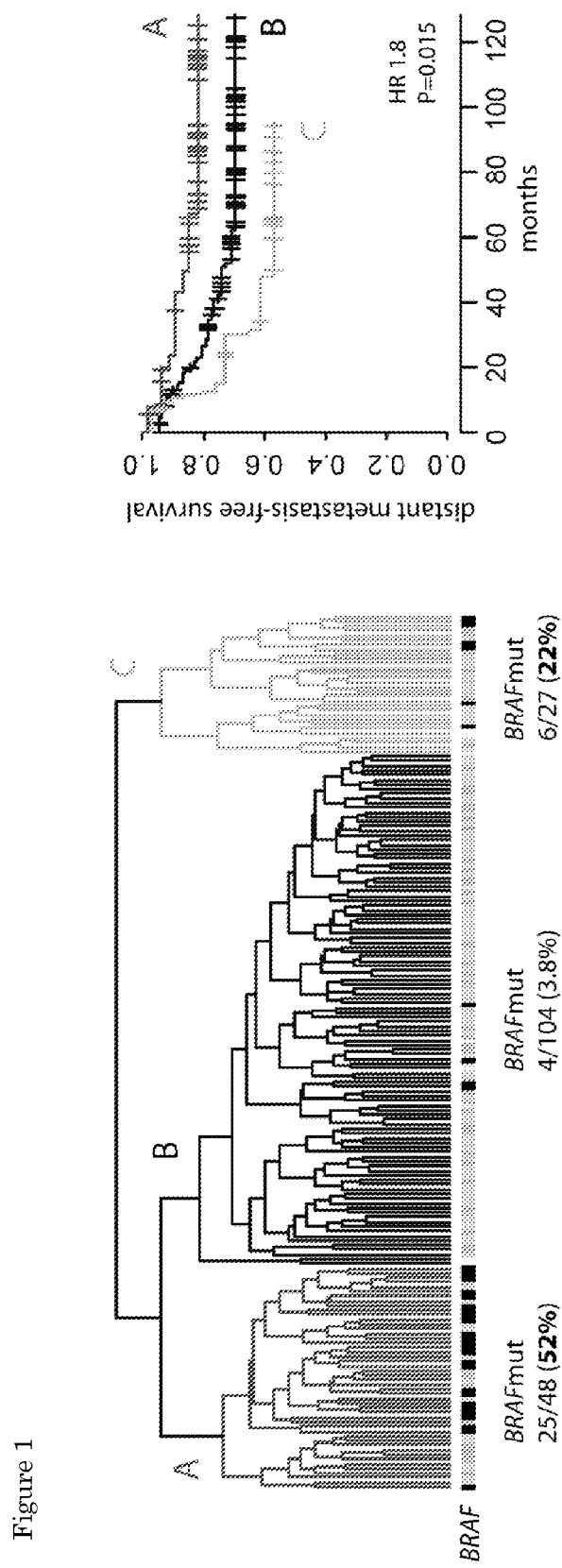

Zhang Fan, et al.—Cross-Study Validation and Combined Analysis of Microarray Data for Cancer Using Vector Cosine Angle Method—2005 IEEE Engineering in Medicine and Biology 27th Annual Conference, Shanghai, China, Sep. 1-4, 2005—pp. 4810-4813—© 2005 IEEE.

Laura J. Van 'T Veer, et al.—Gene expression profiling predicts clinical outcome of breast cancer—Nature—vol. 415, Jan. 31, 2002, pp. 530-536—© 2002 Macmillan Magazines Ltd.

Chih-Chung Chang, et al.—LIBSVM: a Library for Support Vector Machines (Version 2.31)—http://www.csie.ntu.edu.tw/~cjlin/libsvm—Sep. 7, 2001—Department of Computer Science and Information Engineering, National Taiwan University, Taipei 106, Taiwan.

Isabel Gonzalez-Garcia, et al.—Standardized Approach for Microsatellite Instability Detection in Colorectal Carcinomas—Journal of the National Cancer Institute, vol. 92, No. 7, Apr. 5, 2000, pp. 544-549.

Agilent Whole Human Genome Oligo Microarray Kit with SurePrint Technology—Agilent Whole Genome 44k microarray—Agilent Technologies—Catalog 60-mer Oligo—© Agilent Technologies, Inc. 2004, Jul. 15, 2004.

Agilent Feature Extraction Software (v9.5)—Reference Guide—Research Use Only—Agilent Technologies—© Agilent Technologies, Inc. 2007—Fourth Edition, Feb. 2007—Printed in USA.

Lee Weng, et al.—Rosetta error model for gene expression analysis—Bioinformatics—vol. 22, No. 9, 2006, pp. 1111-1121—© The Author 2006. Published by Oxford University Press.

Richard Simon, et al.—Analysis of Gene Expression Data Using BRB-Array Tools—Cancer Informatics—2007:3 pp. 11-17.

Yixin Wang, et al.—Gene Expression Profiles and Molecular Markers to Predict Recurrence of Dukes' B Colon Cancer—Journal of Clinical Oncology—vol. 22, No. 9, May 1, 2004, pp. 1564-1571—© 2004 American Society of Clinical Oncology.

Francois Bertucci, et al.—Gene expression profiling of colon cancer by DNA microarrays and correlation with histoclinical parameters—Oncogene—vol. 23, No. 7, pp. 1377-1391—© 2004 Nature Publishing Group.

Diego Arango, et al.—Gene-Expression Profiling Predicts Recurrence in Duke's C Colorectal Cancer—Gastroenterology 2005—vol. 129, No. 3, pp. 874-884—©2005 American Gastroenterological Association (AGA) and © 2005 Elsevier Science.

Wade S. Samowitz, et al.—Poor Survival Associated with the BRAF V600E Mutation in Microsatellite-Stable Colon Cancers—Cancer Research—vol. 65, No. 14, pp. 6063-6070—© 2005 American Association for Cancer Research—Baltimore, MD, US.

Katherine S. Garman, et al.—A genomic approach to colon cancer risk stratification yields biologic insights into therapeutic opportunities—Proceedings of the National Academy of Sciences (PNAS)—vol. 105, No. 49, Dec. 9, 2008, pp. 19432-19437.

Alain Barrier, et al.—Stage II Colon Cancer Prognosis Prediction by Tumor Gene Expression Profiling—Journal of Clinical Oncology—vol. 24, No. 29, Oct. 10, 2006, pp. 4685-4691—© 2006 American Society of Clinical Oncology.

Kuebler et al., Oxaliplatin combined with weekly bolus fluorouracil and leucovorin as surgical adjuvant chemotherapy for stage II and III colon cancer: Results from NSABP C-07, Journ. of Clin. Oncology, vol. 25, No. 16, pp. 2198-2204 (2007).

Quasar et al., Adjuvant chemotherapy versus observation in patients with colorectal cancer: a randomised study, The Lancet, vol. 270, Issue 9604, pp. 2020-2029 (2007).

* cited by examiner

METHODS AND MEANS FOR TYPING A SAMPLE COMPRISING COLORECTAL CANCER CELLS

This application is the U.S. National Phase of, and Applicants claim priority from, International Patent Application Number PCT/NL2009/050797 filed 23 Dec. 2009 and European Patent Application Number 08172911.3 filed 24 Dec. 2008, each of which are incorporated herein by reference.

BACKGROUND OF THE INVENTION

The invention relates to the field of oncology. More specifically, the invention relates to a method for typing colorectal cancer cells. The invention provides means and methods for differentiating colorectal cancer cells with a low metastasizing potential and with a high metastatic potential.

Worldwide over a million new cases of colorectal cancer were diagnosed in 2002, accounting for more than 9% of all new cancer cases (Ries et al., editors. National Cancer Institute Bethesda, Md. 2006. May 3, 2006. SEER Cancer Statistics Review, 1975-2003). Colorectal cancer is the third most common cancer worldwide after lung and breast with two-thirds of all colorectal cancers occurring in the more developed regions. As with all cancers, chances of survival are good for patients when the cancer is detected in an early stage. Stage I patients have a survival rate of ~93% while the 5-year survival rate drops to ~80% in stage II patients and to 60% in stage III patients (Sobrero et al., 2006. The Lancet Oncology 7(6): 515-517).

Despite numerous clinical trials, the benefit of adjuvant chemotherapy for stage II colon cancer patients is still debatable (Andre et al., 2006. Annals of Surgical Oncology 13(6): 887-898). Several analyses and meta-analyses have been performed of clinical trials comparing adjuvant therapy with observation in patients with stage II colon or colorectal cancer (for review, see Benson et al., 2004. Journal of Clinical Oncology 22: 3408-3419). Three-fourth of patients is cured by surgery alone and therefore, less than 25% of patients would benefit from additional chemotherapy. As a result, the number of patients receiving adjuvant chemotherapy varies significantly amongst developed countries and the official guidelines give no clear recommendation (Van Cutsem et al., 2005. Annals of Oncology 16 (suppl_1):i18-i19). For stage III patients, adjuvant treatment is recommended for all patients (Gill et al., 2004. Journal of Clinical Oncology 22: 1797-1806) although patients with T1 or T2 N1 MO tumors (stage IIIA) have a significantly better survival rate than stage II B patients indicating that many patients would not require additional chemotherapy.

The identification of the sub-group of patients that are more likely to suffer from a recurrent disease would therefore allow the identification of patients who are more likely to benefit from adjuvant treatment after surgery. Much effort has been put on the identification of clinico-pathological parameters that predict prognosis. The most important factors for predicting the risk of recurrence are emergency presentation, poorly differentiated tumor (histological grade) and depth of tumor invasion and adjacent organ involvement (T4) (Van Cutsem et al., 2005. Annals of Oncology 16 (suppl_1):i18-i19; Le Voyer et al., 2003. Journal of Clinical Oncology 21: 2912-2919). Assessment of an inadequate number of lymph node is an additional risk factor as low numbers of examined lymph nodes is associated with a decreased 5-year survival rate. Although these clinical parameters have been shown to correlate to outcome, physicians acknowledge that they are insufficient to correctly identify high risk patients.

Current pathological prediction factors are not sufficient to identify "high risk" patients, who have an increased risk for recurrent disease. It is therefore an object of the present invention to provide methods and means to allow typing of cancer samples from patients suffering from colorectal cancer to identify said high risk patients and low risk patients.

DESCRIPTION OF THE INVENTION

Therefore, the invention provides a method for typing a RNA sample of an individual suffering from colorectal cancer or suspected of suffering there from, the method comprising providing an RNA sample that is prepared from a tissue sample from said individual, said tissue sample comprising colorectal cancer cells or suspected to comprise colorectal cancer cells; determining RNA levels for a set of genes in said RNA sample; and typing said RNA sample on the basis of the RNA levels determined for said set of genes; wherein said set of genes comprises at least two of the genes listed in Table 1.

This study discloses a robust gene expression signature that predicts disease relapse and be added to current clinico-pathological risk assessment to assist physicians in making treatment decisions. The identification of the sub-group of patients that are more likely to suffer from a recurrent disease allows the identification of patients who are more likely to benefit from adjuvant chemotherapy and should be treated after surgery.

The present gene expression signature was identified after removing to a large extent training samples comprising cancer cells with an activating mutation in B-Raf (BRAFmut). BRAFmut colon cancer samples were found to be highly variable in gene expression data which masked more general, prognosis-related gene expression data. Without being bound by theory, said variable gene expression might be caused by a high degree of micro-satellite instability (MSI) in BRAFmut colon cancer samples. The resultant gene expression signature that was identified after removing the BRAFmut colon cancer samples was found to be robust and applicable to a sample comprising cancer cells with and without BRAFmut.

Colorectal cancer is a type of cancer that originates in the large intestine or bowel, comprising the colon and the rectum. Colon cancer and rectal cancer have many features in common. The majority of colorectal cancers are adenocarcinomas. These are cancers of the cells that line the inside layer of the wall of the colon and rectum. Other less common types of tumors may also develop in the colon and rectum, such as carcinoid tumors, which develop from specialized hormone-producing cells of the intestine; gastrointestinal stromal tumors or leiomyosarcomas, which develop from smooth muscle cells in the wall of the intestine; and lymphomas, which are cancers of immune system cells that typically develop in lymph nodes but also may start in the colon and rectum or other organs.

Adenocarcinomas usually start as a colorectal polyp, a hyperplasia which is defined as a visible protrusion above the surface of the surrounding normal large bowel mucosa. Colorectal polyps are classified as either neoplastic (adenomatous polyps) or non-neoplastic, comprising hyperplastic, mucosal, inflammatory, and hamartomatous polyps which have no malignant potential. Adenomatous polyps, or adenomas, are attached to the bowel wall by a stalk (pedunculated) or by a broad, flat base (sessile). A colorectal hyperplasia or polyp can develop into a malignant adenocarcinoma.

Using RNA isolated from a training set of colorectal samples with a wild type B-Raf gene and comprising samples from colorectal cancers that did not give rise to metastases in patients within the length of follow up time of each patient;

and samples from colorectal cancers that gave rise to metastases in patients within the length of follow up time of each patient, genes were selected using a multivariate Cox Regression based method (Simon et al., Design and Analysis of DNA Microarray Investigations, Springer-Verlag New York, (2003); Korn et al., Journal of Statistical Planning and Inference 124, 379-398 (2004)). Genes were selected of which the RNA levels was significantly related to survival of the patient, independent of patient stage, where survival is defined as being free of cancer recurrence. Each of the genes listed in Table 1 was shown to be predictive of survival and have a minimum significance threshold of 0.001.

In a preferred embodiment, a set of at least two genes comprises MCTP1 (SEQ ID NO 36) and THNSL2 (SEQ ID NO 13). More preferred is the determination of a ratio of expression of MCTP1 (SEQ ID NO 36) and THNSL2 (SEQ ID NO 13). A sample with a determined MCTP1/THNSLC2 ratio above a predetermined threshold is indicative of a sample with a low risk of cancer recurrence. Samples with a high MCTP1/THNSLC2 ratio (low-risk) showed a 5-year distant metastasis free survival (DMSF) of 87%. Samples with a low MCTP1/THNSLC2 ratio (high-risk) showed a DMFS of 70%.

In a preferred embodiment, a set of genes according to the invention comprises at least three of the genes listed in Table 1, more preferred at least four of the genes listed in Table 1, more preferred at least five of the genes listed in Table 1, more preferred at least six of the genes listed in Table 1, more preferred at least seven of the genes listed in Table 1, more preferred at least eight of the genes listed in Table 1, more preferred at least nine of the genes listed in Table 1, more preferred at least ten of the genes listed in Table 1, more preferred at least fifteen of the genes listed in Table 1, more preferred at least twenty of the genes listed in Table 1, more preferred at least twenty-five of the genes listed in Table 1, more preferred at least thirty of the genes listed in Table 1, more preferred at least forty of the genes listed in Table 1, more preferred at least fifty of the genes listed in Table 1, more preferred at least sixty of the genes listed in Table 1, more preferred at least seventy of the genes listed in Table 1, more preferred at least eighty of the genes listed in Table 1, more preferred hundred of the genes listed in Table 1, more preferred hundred-fifty of the genes listed in Table 1, more preferred two-hundred of the genes listed in Table 1, more preferred all of the genes listed in Table 1.

A preferred set of genes for use in a method of the invention comprises the first two rank-ordered genes listed in Table 1, more preferred the first three rank-ordered genes, more preferred the first four rank-ordered genes, more preferred the first five rank-ordered genes, more preferred the first six rank-ordered genes, more preferred the first seven rank-ordered genes, more preferred the first eight rank-ordered genes, more preferred the first ten rank-ordered genes, more preferred the first fifteen rank-ordered genes, more preferred the first twenty rank-ordered genes, more preferred the first thirty rank-ordered genes, more preferred the first forty rank-ordered genes, more preferred the first fifty rank-ordered genes, more preferred the first sixty rank-ordered genes, more preferred the first seventy rank-ordered genes, more preferred the first eighty rank-ordered genes, more preferred the first ninety rank-ordered genes, more preferred the first hundred rank-ordered genes, more preferred the first hundred-fifty rank-ordered genes, more preferred the first two-hundred rank ordered genes, more preferred all two hundred and nine genes listed in Table 1.

A further preferred signature comprises genes referred to in Table 1 as ZBED4, LIF, PIM3, IL2RA, PYROXD1, CTSC, EDEM1, M6PRBP1, SLC6A12, THNSL2, PPARA, ZNF697, LAMA3, CA438802, MCTP1, HSD3B1, CYFIP2, IL2RB, also referred to as "18 gene profile".

A further preferred signature comprises genes referred to in Table 1 as ZBED4, LIF, IL18R1, PIM3, IL2RA, PYROXD1, CTSC, EDEM1, M6PRBP1, SLC6A12, THNSL2, KCNJ10, THC2663361, C10orf67, KIAA0040, BC040628, AK096685, PIGW, PPARA, COLQ, AK021427, C15orf27, PRDM4, LOC165186, ZNF697, CRYGA, EEPD1, LAMA3, NEDD8, CA438802, MCTP1, HSD3B1, CYFIP2, IL2RB, XKR3, NT_035113, THC2520461, and THC2662025.

A cell sample is a clinically relevant sample that comprises a colorectal cancer cell or an expression product comprising a nucleic acid from a colorectal cancer cell.

In a preferred embodiment, a cell sample according to the invention is obtained directly from the large intestine during surgery. In an alternative embodiment, the cell sample is prepared from a biopsy sample that is taken during colonoscopy.

It is further preferred that the biopsies have a depth of at most 10 millimeter, more preferred at most 5 millimeter, with a preferred diameter of about 2 millimeter, more preferred about 3 millimeter, more preferred about 4 millimeter, more preferred about 5 millimeter, more preferred about 6 millimeter, more preferred about 7 millimeter, more preferred about 8 millimeter, more preferred about 9 millimeter, more preferred about 10 millimeter. However, other forms that are equal in size and total volume are also possible.

In another preferred embodiment, the tissue sample comprises stool or blood voided by a patient suffering from colorectal cancer, said tissue sample comprising a colorectal cancer cell or a gene expression product such as a nucleic acid product from a colorectal cancer cell. Methods to purify cells or gene expression products such as RNA from human stool or blood samples are known in the art and have been described for example in patent application WO199820355, WO2003068788, and Yang et al. 2005. Cancer Lett 226: 55-63, which are herein enclosed by reference.

Samples can be processed in numerous ways, as is known to a skilled person. For example, they can be freshly prepared from cells or tissues at the moment of harvesting, or they can be prepared from samples that are stored at −70° C. until processed for sample preparation. Alternatively, tissues, biopsies, stool or blood samples can be stored under conditions that preserve the quality of the protein or RNA. Examples of these preservative conditions are fixation using e.g. formaline, RNase inhibitors such as RNAsin (Pharmingen) or RNasecure (Ambion), aquous solutions such as RNAlater (Assuragen; U.S. Pat. No. 6,204,375), Hepes-Glutamic acid buffer mediated Organic solvent Protection Effect (HOPE; DE10021390), and RCL2 (Alphelys; WO04083369), and non-aquous solutions such as Universal Molecular Fixative (Sakura Finetek USA Inc.; U.S. Pat. No. 7,138,226).

The RNA level of at least two of the genes listed in Table 1 can be determined by any method known in the art. Methods to determine RNA levels of genes are known to a skilled person and include, but are not limited to, Northern blotting, quantitative PCR, and microarray analysis.

Northern blotting comprises the quantification of the nucleic acid expression product of a specific gene by hybridizing a labeled probe that specifically interacts with said nucleic acid expression product, after separation of nucleic acid expression products by gel electrophoreses. Quantification of the labeled probe that has interacted with said nucleic acid expression product serves as a measure for determining the level of expression. The determined level of expression can be normalized for differences in the total amounts of nucleic acid expression products between two separate samples by comparing the level of expression of a gene that is known not to differ in expression level between samples.

Quantitative Polymerase Chain Reaction (qPCR) provides an alternative method to quantify the level of expression of nucleic acids. qPCR can be performed by real-time PCR (rtPCR), in which the amount of product is monitored during the reaction, or by end-point measurements, in which the amount of a final product is determined. As is known to a skilled person, rtPCR can be performed by either the use of a nucleic acid intercalator, such as for example ethidium bromide or SYBR® Green I dye, which interacts which all generated double stranded products resulting in an increase in fluorescence during amplification, or by the use of labeled probes that react specifically with the generated double stranded product of the gene of interest. Alternative detection methods that can be used are provided by dendrimer signal amplification, hybridization signal amplification, and molecular beacons.

Different amplification methods, known to a skilled artisan, can be employed for qPCR, including but not limited to PCR, rolling circle amplification, nucleic acid sequence-based amplification, transcription mediated amplification, and linear RNA amplification.

For the simultaneous detection of multiple nucleic acid gene expression products, qPCR methods such as reverse transcriptase-multiplex ligation-dependent amplification (rt-MLPA), which accurately quantifies up to 45 transcripts of interest in a one-tube assay (Eldering et al., Nucleic Acids Res 2003; 31: e153) can be employed.

Microarray-based analyses involve the use of selected biomolecules that are immobilized on a surface. A microarray usually comprises nucleic acid molecules, termed probes, which are able to hybridize to nucleic acid expression products. The probes are exposed to labeled sample nucleic acid, hybridized, and the abundance of nucleic acid expression products in the sample that are complementary to a probe is determined. The probes on a microarray may comprise DNA sequences, RNA sequences, or copolymer sequences of DNA and RNA. The probes may also comprise DNA and/or RNA analogues such as, for example, nucleotide analogues or peptide nucleic acid molecules (PNA), or combinations thereof. The sequences of the probes may be full or partial fragments of genomic DNA. The sequences may also be in vitro synthesized nucleotide sequences, such as synthetic oligonucleotide sequences.

It is preferred that said RNA levels are determined simultaneously. Simultaneous analyses can be performed, for example, by multiplex qPCR and microarray analysis. Microarray analyses allow the simultaneous determination of the nucleic acid levels of expression of a large number of genes, such as more than 50 genes, more than 100 genes, more than 1000 genes, or even more than 10.000 genes, allowing the use of a large number of gene expression data for normalization of the genes comprising the colorectal expression profile.

In a preferred embodiment, therefore, said RNA levels are determined by microarray analysis.

Said probe is specific for a gene listed in Table 1. A probe can be specific when it comprises a continuous stretch of nucleotides that are completely complementary to a nucleotide sequence of a RNA product of said gene, or a cDNA product thereof. A probe can also be specific when it comprises a continuous stretch of nucleotides that are partially complementary to a nucleotide sequence of a RNA product of said gene, or a cDNA product thereof. Partially means that a maximum of 5% from the nucleotides in a continuous stretch of at least 20 nucleotides differs from the corresponding nucleotide sequence of a RNA product of said gene. The term complementary is known in the art and refers to a sequence that is related by base-pairing rules to the sequence that is to be detected. It is preferred that the sequence of the probe is carefully designed to minimize nonspecific hybridization to said probe. It is preferred that the probe is or mimics a single stranded nucleic acid molecule. The length of said complementary continuous stretch of nucleotides can vary between 15 bases and several kilo bases, and is preferably between 20 bases and 1 kilobase, more preferred between 40 and 100 bases, and most preferred 60 nucleotides. A most preferred probe comprises a continuous stretch of 60 nucleotides that are identical to a nucleotide sequence of a RNA product of a gene, or a cDNA product thereof.

To determine the RNA level of at least two of the genes listed in Table 1, the RNA sample is preferably labeled, either directly or indirectly, and contacted with probes on the array under conditions that favor duplex formation between a probe and a complementary molecule in the labeled RNA sample. The amount of label that remains associated with a probe after washing of the microarray can be determined and is used as a measure for the level of RNA of a nucleic acid molecule that is complementary to said probe.

The determined RNA levels for at least two genes listed in Table 1 can be normalized to correct for systemic bias. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment. To reduce systemic bias, the determined RNA levels are preferably corrected for background non-specific hybridization and normalized using, for example, Feature Extraction software (Agilent Technologies). Other methods that are or will be known to a person of ordinary skill in the art, such as a dye swap experiment (Martin-Magniette et al., Bioinformatics 21:1995-2000 (2005)) can also be applied to normalize differences introduced by dye bias. Normalization of the expression levels results in normalized expression values.

Conventional methods for normalization of array data include global analysis, which is based on the assumption that the majority of genetic markers on an array are not differentially expressed between samples [Yang et al., Nucl Acids Res 30: 15 (2002)]. Alternatively, the array may comprise specific probes that are used for normalization. These probes preferably detect RNA products from housekeeping genes such as glyceraldehyde-3-phosphate dehydrogenase and 18S rRNA levels, of which the RNA level is thought to be constant in a given cell and independent from the developmental stage or prognosis of said cell.

Therefore, a preferred method according to the invention further comprises normalizing the determined RNA levels of said set of at least two of the genes listed in Table 1 in said sample.

Said normalization preferably comprises median centering, in which the "centers" of the array data are brought to the same level under the assumption that the majority of genes are un-changed between conditions. Said normalization preferably comprises Lowess (LOcally WEighted Scatterplot Smoothing) local regression normalization to correct for both print-tip and intensity-dependent bias.

In a preferred embodiment, genes are selected of which the RNA levels are largely constant between different tissue samples comprising colorectal cells from one individual, and between tissue samples comprising colorectal cells from different individuals. It is furthermore preferred that RNA levels of said set of normalization genes differ between the genes. For example, it is preferred to select genes with a low RNA level in said tissue sample, and genes with a high RNA level. More preferred is to select genes with a low RNA level in said tissue sample, genes with a moderate RNA level, and genes with a high RNA level. It will be clear to a skilled artisan that the RNA levels of said set of normalization genes preferably allow normalization over the whole range of RNA levels.

A preferred method further comprises multiplying each of the normalized expression values with a predetermined constant for said gene to obtain a weighted value for the relative RNA level of said gene, and thereby a set of weighted values for said set of genes, said method further comprising typing said sample on the basis of said set of weighted values.

Said set of weighted values can be summed and compared to a summed set of weighted values from a reference sample. It is preferred that said summed set of weighted values is compared to a classification threshold, that is determined by the values obtained from RNA samples of which the typing is known.

Colorectal cancers such as adenocarcinomas are staged dependent on the visible invasiveness of the surrounding tissue. A staging system is provided by the TNM Staging System, which combines data about the Tumor (T), the spread to lymph nodes (N), and the existence of distant metastases (M). A TNM stage I colorectal cancer is defined as a cancer that began to spread and has invaded the submucosa or the muscularis propria. A. TNM stage II defines a cancer that has invaded through the muscularis propria into the subserosa, or into the pericolic or perirectal tissues, but has not reached the lymph nodes. A stage III defines a cancer that has spread to the lymph nodes in the absence of distant metastases. A stage IV defines a cancer that has spread to distant sites.

In a preferred embodiment, the invention provides a method of typing an individual suffering from colorectal cancer, wherein said colorectal cancer comprises a TNM stage I, TNM stage II or TNM stage III colorectal cancer as determined by the TNM Staging System, wherein TNM stage II and TNM stage III are preferred colorectal cancers.

It is preferred that said typing in a method according to the invention allows differentiating cancer cells with a low metastasizing potential or risk of cancer recurrence and cancer cells with a high metastatic potential or risk of cancer recurrence.

To differentiate cancer cells with a low metastasizing potential and cancer cells with a high metastatic potential, the RNA levels at least two of the genes listed in Table 1 can be compared to RNA levels of said genes in a reference sample.

A reference sample is preferably an RNA sample isolated from a colorectal tissue from a healthy individual, or an RNA sample from a relevant cell line or mixture of cell lines. Said reference sample can also be an RNA sample from a cancerous growth of an individual suffering from colorectal cancer. Said individual suffering from colorectal cancer can have an increased risk of cancer recurrence, or a low risk of cancer recurrence.

It is preferred that said reference sample is an RNA sample from an individual suffering from colorectal cancer and having a low risk of cancer recurrence. In a more preferred embodiment, said reference sample is a pooled RNA sample from multiple tissue samples comprising colorectal cells from individuals suffering from colorectal cancer and having a low risk of cancer recurrence. It is preferred that said multiple tissue sample comprises more than 10 tissue samples, more preferred more than 20 tissue samples, more preferred more than 30 tissue samples, more preferred more than 40 tissue samples, most preferred more than 50 tissue samples. A most preferred reference sample comprises pooled RNA from multiple tissue samples comprising colorectal cancer cells from individuals having a low risk of cancer recurrence and from individuals having a high risk of cancer recurrence.

A further preferred reference sample comprises RNA isolated and pooled from colon tissue from healthy individuals, or from so called normal adjacent tissue from colon cancer patients or RNA from a generic cell line or cell line mixture. The RNA from a cell line or cell line mixture can be produced in-house or obtained from a commercial source such as, for example, Stratagene Human Reference RNA.

Typing of a sample can be performed in various ways. In one method, a coefficient is determined that is a measure of a similarity or dissimilarity of a sample with said reference sample. A number of different coefficients can be used for determining a correlation between the RNA expression level in an RNA sample from an individual and a reference sample. Preferred methods are parametric methods which assume a normal distribution of the data. One of these methods is the Pearson product-moment correlation coefficient, which is obtained by dividing the covariance of the two variables by the product of their standard deviations. Preferred methods comprise cosine-angle, un-centered correlation and, more preferred, cosine correlation (Fan et al., Conf Proc IEEE Eng Med Biol Soc. 5:4810-3 (2005)).

Preferably, said correlation with a reference sample is used to produce an overall similarity score for the set of genes that are used. A similarity score is a measure of the average correlation of RNA levels of a set of genes in an RNA sample from an individual and a reference sample. Said similarity score can, for example, be a numerical value between +1, indicative of a high correlation between the RNA expression level of the set of genes in a RNA sample of said individual and said reference sample, and −1, which is indicative of an inverse correlation and therefore indicative of having an increased risk of cancer recurrence (van 't Veer et al., Nature 415: 484-5 (2002)).

In another aspect, the invention provides a method of classifying an individual suffering from colorectal cancer, comprising classifying said individual as having a poor prognosis or a good prognosis by a method comprising determining a similarity value between RNA levels from a set of at least two genes listed in Table 1 in a RNA sample from said individual and a level of expression from said set of genes in a RNA sample from a patient having no recurrent disease within five years of initial diagnosis, and classifying said individual as having a poor prognosis if said similarity value is below a similarity threshold value, and classifying said individual as having a good prognosis if said similarity value exceeds a similarity threshold value.

The present invention provides a set of markers useful for distinguishing samples from colorectal cancer patients with a good prognosis from samples from colorectal cancer patients with a poor prognosis. In a method of the invention the expression level of these markers is used to determine whether an individual afflicted with colon cancer will have a good or poor clinical prognosis. In one embodiment, the invention provides for a method of determining whether an individual afflicted with colon cancer will likely experience a relapse within five years of initial diagnosis (i.e., whether an individual has a poor prognosis) comprising (1) comparing the level of expression of at least two of the genes listed in Table 1 in a sample taken from the individual to the level of the same markers in a control, where the levels of said control represent those found in an individual with a poor prognosis; and (2) determining whether the level of the expression of each gene from said at least two genes in the sample from the individual is significantly different from the control. If no substantial difference is found, the patient has a poor prognosis, and if a substantial difference is found, the patient has a good prognosis. Persons of skill in the art will readily see that said control levels may alternatively represent those found in an individual with a good prognosis. In a more specific embodiment, both controls are run. In case the pool is not pure 'good prognosis' or 'poor prognosis', a set of experiments of individuals with known outcome should be hybridized against the pool to define the expression control levels for the good prognosis and poor prognosis group. Each individual with unknown outcome is hybridized against the same pool and the resulting expression profile is compared to the templates to predict its outcome.

Poor prognosis of colon cancer may indicate that a tumor is relatively aggressive, while good prognosis may indicate that a tumor is relatively non-aggressive.

Therefore, the invention provides for a method of determining a course of treatment of a colon cancer patient, comprising determining whether the level of expression of at least two genes of table 1 correlates with the level of these genes in a sample representing a good prognosis expression pattern or a poor prognosis pattern; and determining a course of treatment, wherein if the expression correlates with the poor prognosis pattern, the tumor is treated as an aggressive tumor.

A preferred method of classifying a sample as either high or low risk for disease recurrence involves the use of a classification template, derived from Support Vector Machine (SVM) training using all genes identified as being correlated with disease progression. Each gene in the template (signature) has a corresponding weighing factor, as determined by the SVM implementation by Chang & Lin (Chih-Chung Chang and Chih-Jen Lin, LIBSVM: a library for support vector machines, 2001. http://www.csie.ntu.edu.tw/~cjlin/libsvm). This algorithm analyses the information contained in the signature genes across all training set samples and constructs a classification template that best separates patients with recurrence from those without. LIBSVM, developed by Chih-Chung Chang and Chih-Jen Lin, is an integrated software for analyzing many problems in supervised classification or regression frameworks.

A similarity threshold value is an arbitrary value that allows discriminating between RNA samples from patients with a high risk of cancer recurrence, and RNA samples from patients with a low risk of cancer recurrence.

Said similarity threshold value is set at a value at which an acceptable number of patients with known metastasis formation within five years after initial diagnosis would score as false negatives above the threshold value, and an acceptable number of patients without known metastasis formation within five years after initial diagnosis would score as false positives below the threshold value.

A similarity score is preferably displayed or outputted to a user interface device, a computer readable storage medium, or a local or remote computer system.

In an alternative embodiment the invention provides a method of classifying an individual suffering from colorectal cancer, comprising classifying said individual as having a poor prognosis or a good prognosis by a method comprising (a) providing an RNA sample from a said individual that is prepared from a tissue sample from said individual, said tissue sample comprising colorectal cancer cells or suspected to comprise colorectal cancer cells; (b) determining a level of RNA for a set of genes comprising at least two of the genes listed in Table 1 in said sample; (c) determining a similarity value between a level of expression from the set of genes in said individual and a level of expression from said set of genes in a patient having no recurrent disease within five years of initial diagnosis; and (d) classifying said individual as having a poor prognosis if said similarity value is below a first similarity threshold value, and classifying said individual as having a good prognosis if said similarity value exceeds said first similarity threshold value.

In a preferred method of the invention, the level of RNA for a set of genes comprising at least two of the genes listed in Table 1 in said sample is normalized. Normalization can be performed by any method known to a skilled artisan, including global analysis and the use of specific probes.

In yet another aspect, the invention provides a method of assigning treatment to an individual suffering from colorectal cancer, comprising classifying said individual as having a poor prognosis or a good prognosis according to a method of the invention, and assigning adjuvant chemotherapy if said individual is classified as having poor prognosis.

A routine treatment for colorectal cancer is surgery, which is followed by additional treatment if said individual is classified as having poor prognosis. Said additional treatment is selected from adjuvant chemotherapy and radiotherapy. Chemotherapy comprises the use of natural or non-natural compounds to eliminate fast-dividing, and therefore susceptible, cancer cells. Chemotherapeutic compounds comprise alkylating agents such as decarbazine and cyclophosphamide; DNA crosslinking agents such as cisplatin and carboplatin; antimetabolitic agents such as methotrexate, 5-fluorouracil (5FU), and mercaptopurine; alkaloidic agents such as taxanes such as paclitaxel and docetaxel, vincristine and vinblastine; topoisomerase inhibitors such as camptothecins and amsacrine; Antibiotics such as anthracycline glycosides such as doxorubicin, daunorubicin, idarubicin, pirarubicin, and epirubicin; mytomycin; polyamine biosynthesis inhibitors such as eflornithine; mycophenolic acid and other inosine monophosphate dehydrogenase inhibitors; and anthrapyrazoles such as mitoxantrone, piroxantrone, and losoxantrone.

The current standard surgical adjuvant treatment for colorectal cancer comprising modified TNM Stage III or higher is FOLFOX 4. FOLFOX combines oxaliplatin, leucovorin, and infusional 5FU. Leucovorin is a drug that is used to enhance the anti-cancer effect of chemotherapy, and especially 5FU. Other therapies uses are XELOX, a combination therapy comprising oxaliplatin and capecitabine; and FOL-FIRI, which combines 5-FU, leucovorin, and irinotecan, a topoisomerase 1 inhibitor. These can be combined with antibody-based therapeutics including but not limited to bevacizumab, which inhibits angiogenesis, cetuximab, an Epidermal Growth Factor Receptor inhibitor, and panitumumab, an Epidermal Growth Factor receptor inhibitor.

A cancer that originates in the colon or rectum is termed a colorectal cancer or bowel cancer. Said cancer comprises colon cancer and rectal cancer. In a preferred embodiment, a colorectal cancer according to the invention relates to a colon cancer. In another preferred embodiment, a colorectal cancer according to the invention relates to a rectal cancer. In yet another aspect, the invention provides a method for typing colorectal cancer cells according to the invention to select patients having an increased chance of responding to therapy. A method of the invention can be instrumental for identifying subsets of colorectal cancer patients who are at risk for certain complications or who preferentially benefit from specific treatments. Information about colorectal subtypes could also substantially improve the design of future colorectal clinical studies by improving patient selection, reducing variability, and focusing on relevant outcome measures.

In a further aspect, the invention provides a method of developing a colorectal gene signature for typing an RNA sample of an individual suffering from colorectal cancer or suspected of suffering there from, comprising determining a set of genes associated with a distant metastasis free survival period in RNA samples obtained from non-microsatellite instability (non-MSI) colorectal cancers, whereby said distant metastasis free period is 2 years, more preferred 3 years, more preferred 4 years, more preferred 5 years, more preferred more than 5 years. Said non-MSI colorectal cancers preferably do not comprise low-level microsatellite instability (MSI-L) colorectal samples. MSI is often caused by mutations in one of the mismatch repair genes MLH1, MSH2, MSH6, or PMS2 and results in high-level microsatellite instability (MSI-high) in tumours of patients. An MSI test is based on mutation analyses in said mismatch repair genes. The invention preferably provides a method of developing a colorectal gene signature for typing an RNA sample of an individual suffering from colorectal cancer or suspected of suffering there from, comprising determining a set of genes associated with a distant metastasis free survival period in RNA samples obtained from colorectal cancer samples have a valine at position 600 of B-Raf whereby said distant metastasis free period is 2 years, more preferred 3 years, more preferred 4 years, more preferred 5 years, more preferred more than 5 years.

In yet another aspect, the invention provides an array, comprising between 5 and 12.000 nucleic acid molecules comprising a first set of nucleic acid molecules wherein each nucleic acid molecule of said first set comprises a nucleotide sequence that is able to hybridize to a different gene selected from the genes listed in Table 1. Said first set of nucleotide sequences preferably comprises two nucleotide sequences that are able to hybridize to a different gene selected from the genes listed in Table 1, more preferred three nucleotide sequences that are able to hybridize to a different gene selected from the genes listed in Table 1, more preferred four nucleotide sequences that are able to hybridize to a different gene selected from the genes listed in Table 1, more preferred five nucleotide sequences that are able to hybridize to a different gene selected from the genes listed in Table 1, more preferred six nucleotide sequences that are able to hybridize to a different gene selected from the genes listed in Table 1, more preferred ten nucleotide sequences that are able to hybridize to a different gene selected from the genes listed in Table 1, more preferred eighteen nucleotide sequences that are able to hybridize to a different gene selected from the genes listed in Table 1, more preferred thirty-eight nucleotide sequences that are able to hybridize to a different gene selected from the genes listed in Table 1, more preferred forty-four nucleotide sequences that are able to hybridize to a different gene selected from the genes listed in Table 1, more preferred fifty nucleotide sequences that are able to hybridize to a different gene selected from the genes listed in Table 1, more preferred hundred nucleotide sequences that are able to hybridize to a different gene selected from the genes listed in Table 1, more preferred all two hundred-nine nucleotide sequences that are able to hybridize to a different gene selected from the genes listed in Table 1. In a most preferred embodiment, said array comprises at least the eighteen nucleotide sequences that are able to hybridize to a different gene selected from the genes listed in Table 1, and which are indicated as belonging to the 18 gene profile.

In a preferred embodiment, an array according to the invention further comprises a second set of nucleic acid molecules wherein each nucleic acid molecule of said second set comprises a nucleotide sequence that is able to hybridize to normalization gene, whereby it is preferred that the RNA levels of said normalization genes are dissimilar.

In yet another aspect, the invention provides the use of an array according to the invention for obtaining a colorectal expression profile.

FIGURE LEGENDS

FIG. 1: Unsupervised analysis identifies three colon subclasses.

Figure 2:
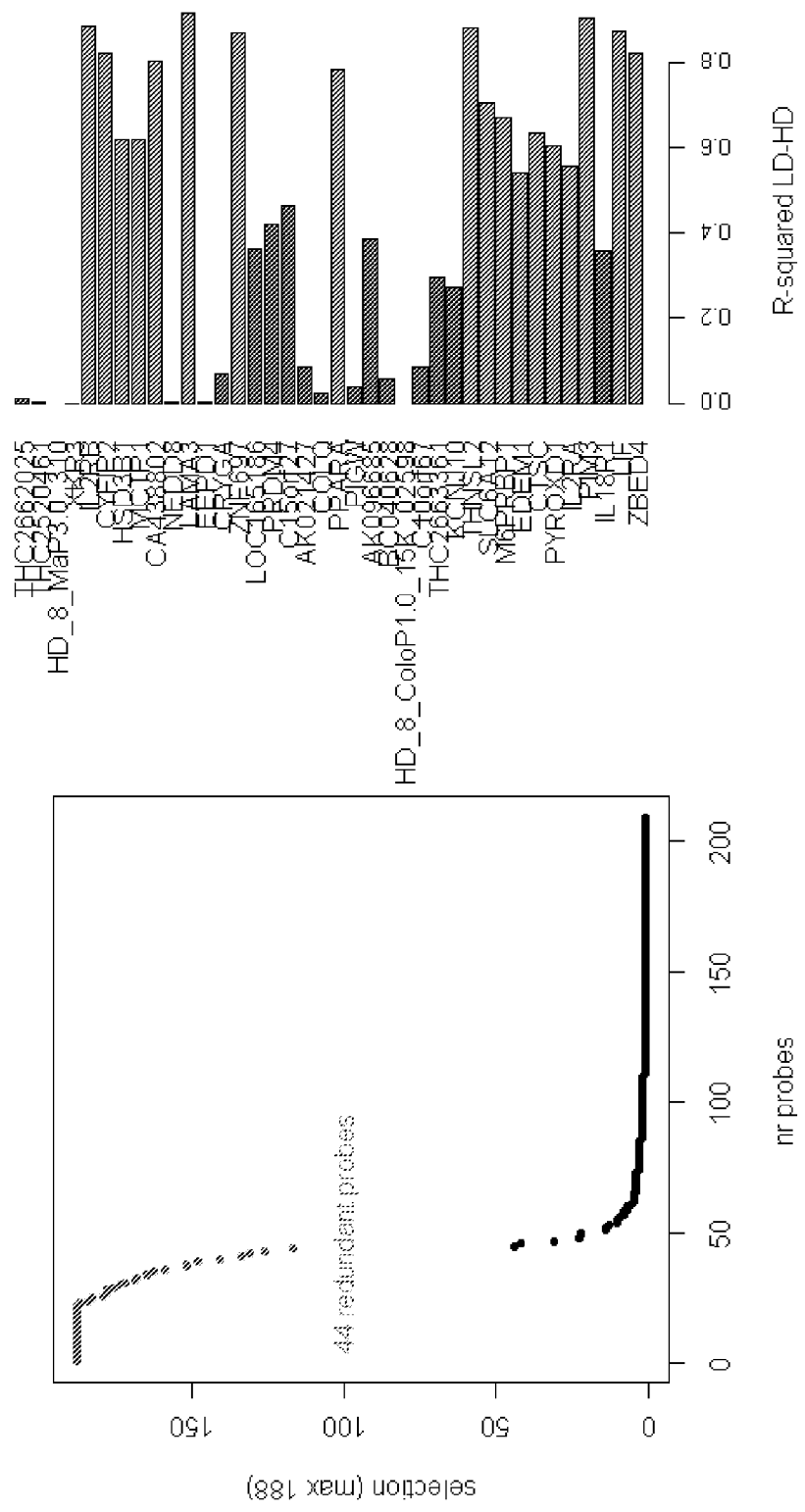

FIG. 2: Scoring of genes for their association with 5-year distant metastasis free survival (DMFS).

Figure 3:
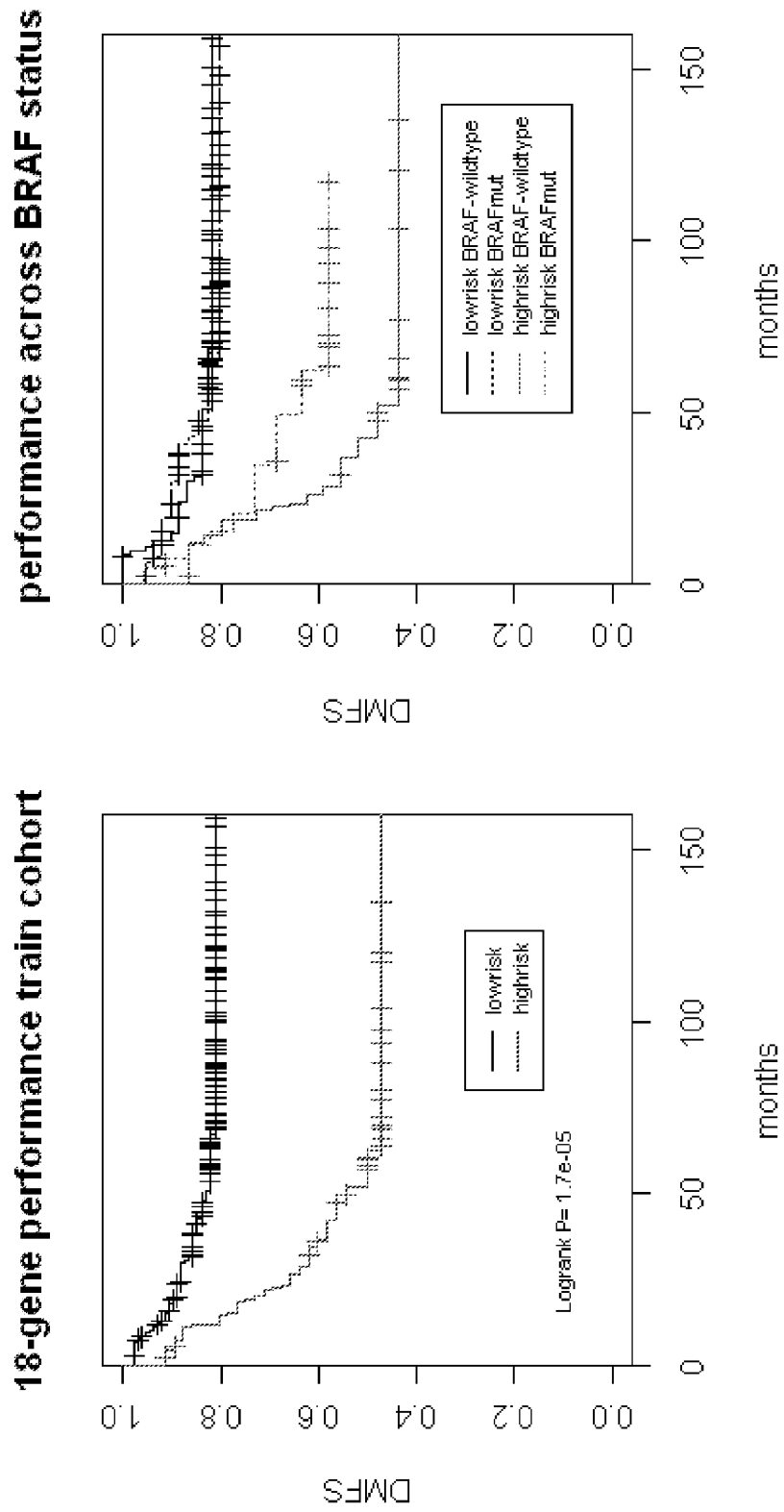

FIG. 3: Kaplan Meier analysis of time to recurrence for 18-gene profile.

Figure 4:
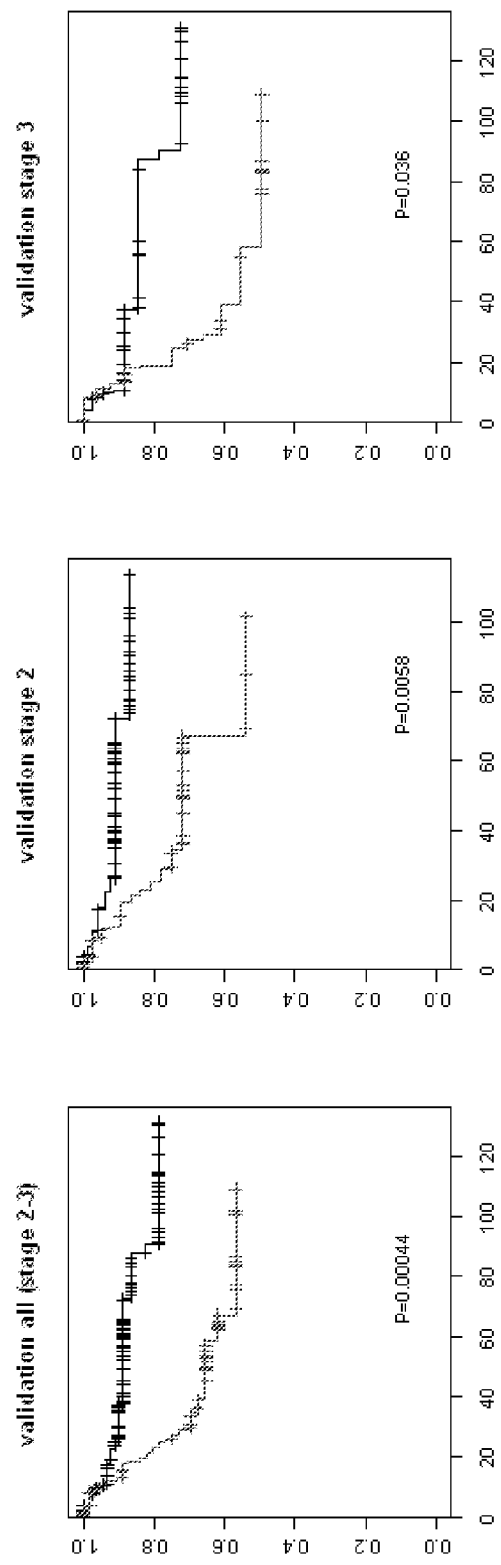

FIG. 4: Kaplan Meier analysis of time to recurrence for 18-gene profile in stage II and III colon samples.

Figure 5:
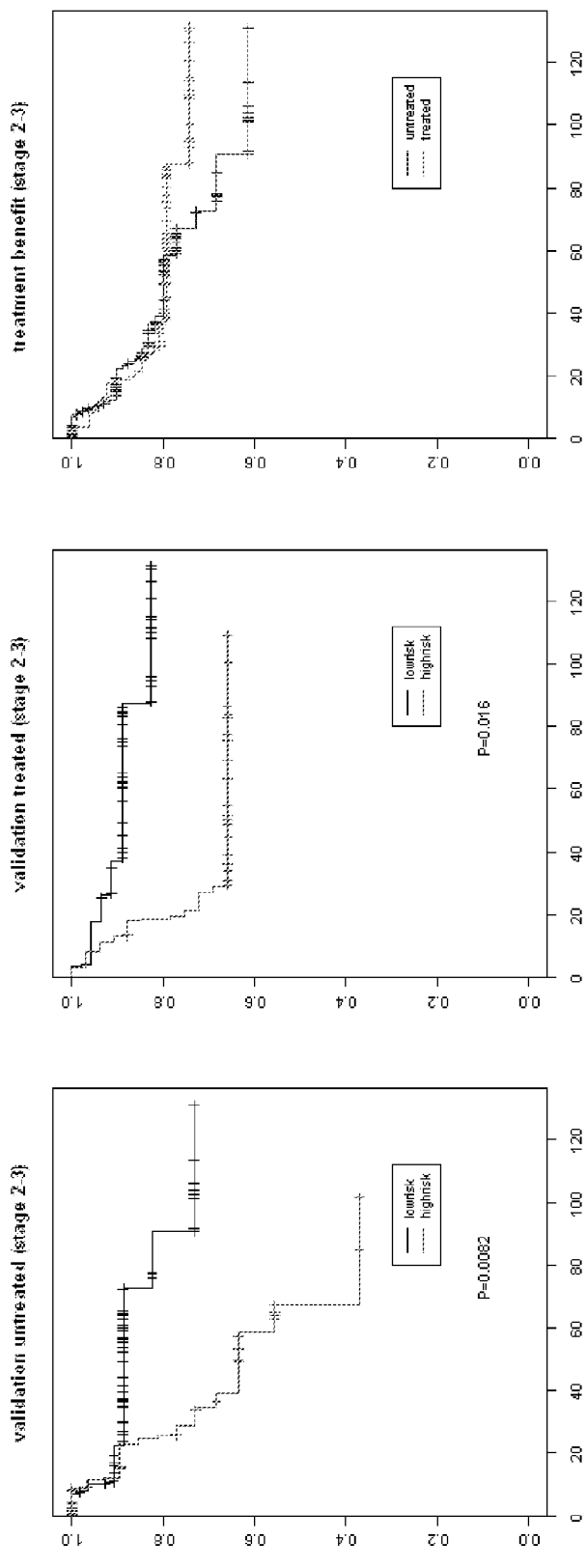
Figure 6:
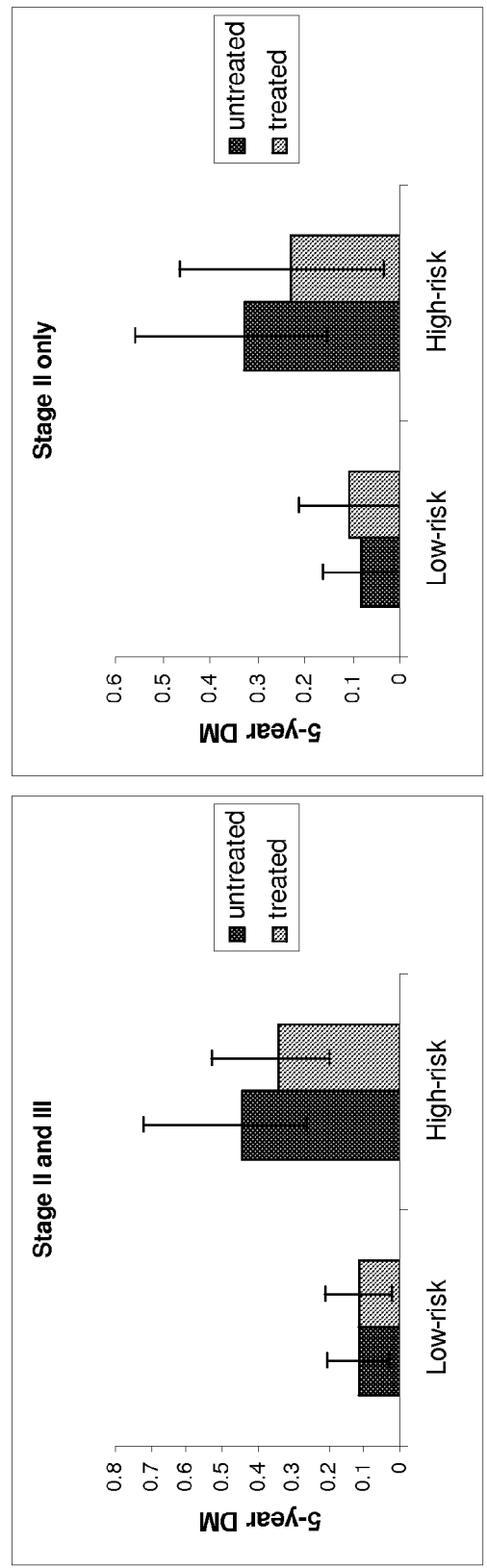

FIG. 5: Kaplan Meier analysis of time to recurrence for 18-gene profile in treated and untreated colon samples FIG. 6: Treatment benefit on low-risk and high-risk patients within validation cohort.

Figure 7:
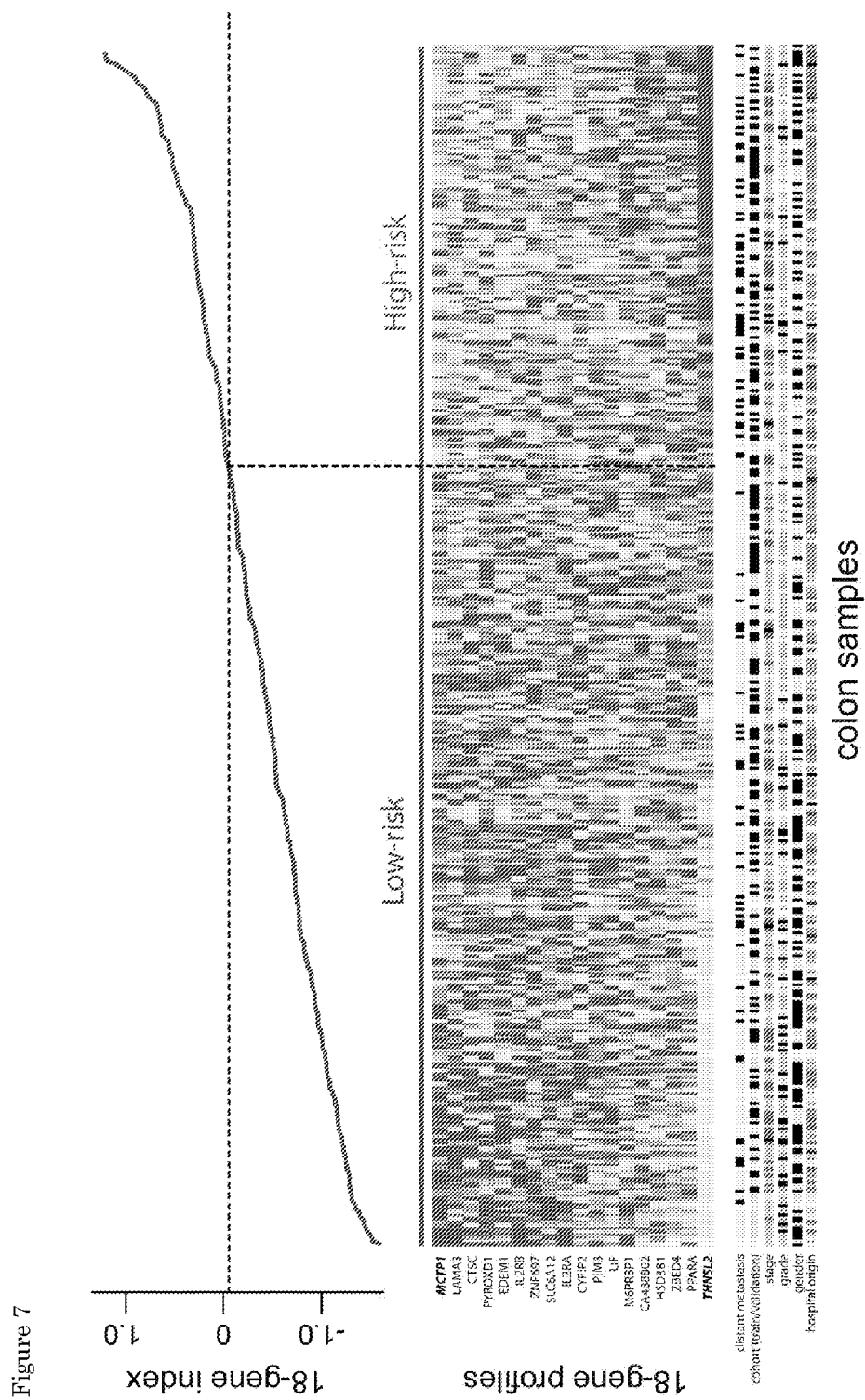

FIG. 7: Differentiation between samples classified as low-risk and high-risk by 18 gene profile.

Figure 8:
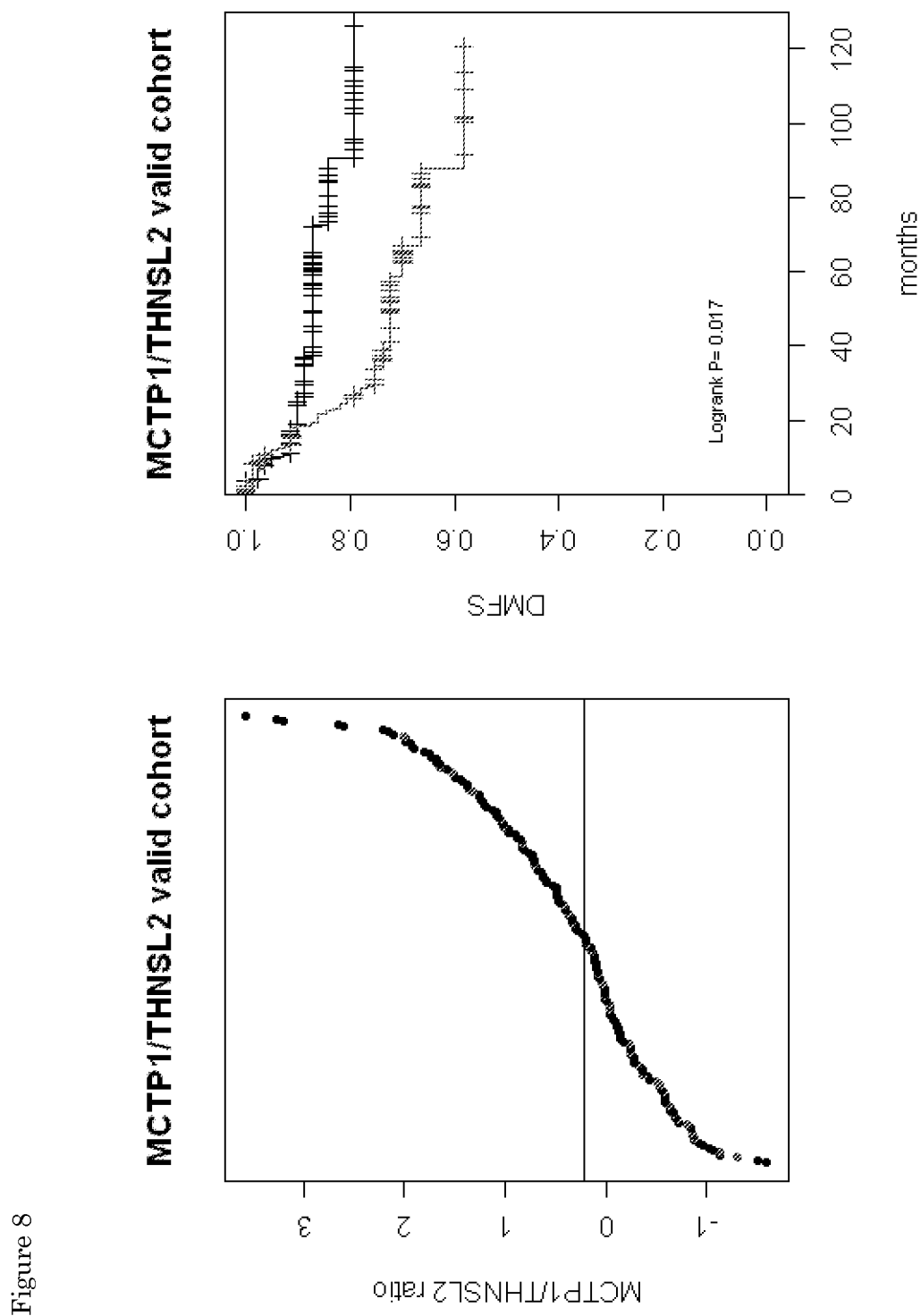

FIG. 8: Use of a MCTP1/THNSL2 ratio for colon prognosis.

Figure 9:
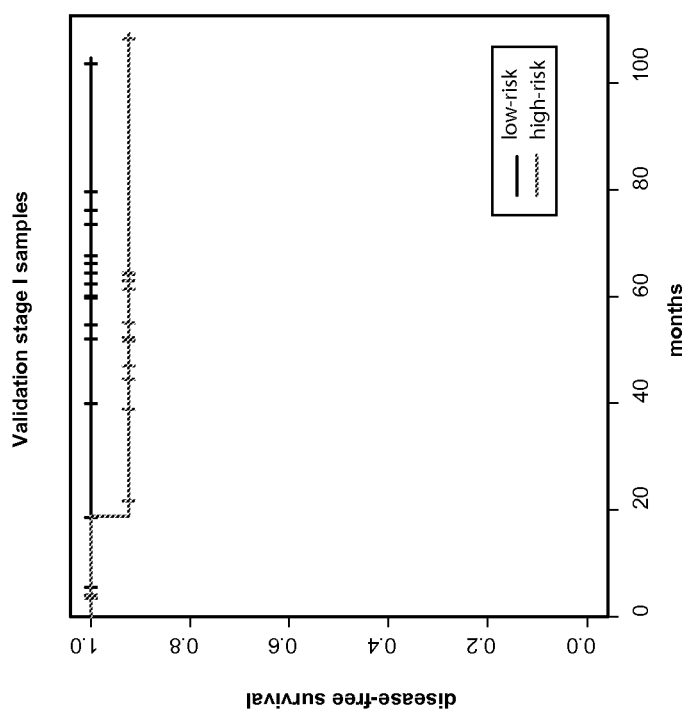

FIG. 9: Kaplan Meier analysis of time to recurrence in stage I colon samples using the 18-gene profile

EXAMPLES

Example 1

Generation of Classifier

Patients

Clinical and pathological information documented at the time of surgery included stage, grade, size and location of tumors. Additionally, the number of lymph nodes assessed for nodal involvement was described in 95% of cases. Tumors were staged according to the TMN staging system. All tissue samples were collected from patients with appropriate informed consent. The study was carried out in accordance with the ethical standards of the Helsinki Declaration and was approved by the Medical Ethical Board of the participating medical centers and hospitals. Patients were monitored for survival and recurrence for up to 270 months.

Mutational analysis

Mutation analysis was performed on all samples, including training set and validation set, using a sequencing approach. B-Raf mutations were analyzed in exon 15 after amplification of cDNA to detect a V600E activating mutation. Primers used were (primer 1) 5'-tgatcaaacttatagatattgcacga (SEQ ID NO: 210) and (primer 2) 5'- tcatacagaacaattccaaatgc (SEQ ID NO: 211). Amplified products were purified using a 96-well ultra-filtration kit for PCR clean-up NUCLEOFAST® Macherey-Nagel. Samples comprising a V600E activating mutation in B-Raf were to a large extent removed from the training set of samples.

MicroSatellite Instability (MSI) Status

MSI status was determined for 145 patients (n=90 in Training Set and n=55 in Validation Set) by as previously described (Gonzalez-Garcia et al. 2000. J Natl Cancer Inst 92: 5423). Briefly, six microsatellite DNA regions were amplified by polymerase chain reaction (PCR) from paired normal and tumor tissues, and products were resolved on denaturing polyacrylamide sequencing gels. The stability of each microsatellite was scored according to the absence (stable) or the presence (unstable) of mobility-shifted bands or additional bands in tumor DNA compared with normal DNA. When the band pattern was difficult to interpret or no amplification product from the normal or tumor DNA was obtained, the sample was scored as not analyzed. Samples from 22 patients were classified as MSI-High (MSI-H).

Microarray Hybridization

Aliquots of total RNA from frozen tumor samples were available for this study. Two-hundred nanogram total RNA was amplified using the Low RNA Input Fluorescent Labeling Kit (Agilent Technologies). Cyanine 3-CTP or Cyanine 5-CTP (GE Health Care) was directly incorporated into the cRNA during in vitro transcription. A total of 750 ng of Cyanine-labeled RNA was co-hybridized with a standard reference to Agilent 44k oligo nucleotide microarrays at 60 degrees Celsius for 17 hrs and subsequently washed according to the Agilent standard hybridization protocol (Agilent Oligo Microarray Kit, Agilent Technologies).

Said standard reference (colon reference pool) comprised 44 colorectal cancer samples, of which 13 were obtained from patients who developed metastasis within 5 years after surgery, and 31 were obtained from patients who did not develop metastasis within 5 years after surgery.

Microarray Image Analysis

Fluorescence intensities on scanned images were quantified, values corrected for background non-specific hybridization, and normalized using Agilent Feature Extraction software (Version 9.5.1.3) according to the manufactures recommended settings for the Agilent Whole Genome 44k microarray. The default normalisation procedure for this microarray includes a linear and a Lowess component, which corrects for any difference in Cy3/5 dye incorporation and centers the final profile at 0 (log 10 scale, Cy5/Cy3). This process is described in the Agilent Feature Extraction Reference Guide. Other custom normalization procedures such as, for example, provided in R/Bioconductor software can also be used.

Data Pre-Processing

Normalised gene expression ratios from each hybridisation were combined to produce a single gene expression profile, per patient, using Agendia XPrint software (version 1.5.1), or using data analysis procedures available in R/Bioconductor software. To obtain a single expression ratio value for each of the signature genes on the array, an error-weighted mean value was calculated for the probes belonging to the same gene as log 10 or log 2 ratios. To establish appropriate relative weights, the Rosetta error model was used, which corrects for the uncertainties in individual probe measurements (Weng L et al, Bioinformatics 22:1111-21 (2006)). A text file containing normalised, error-weighted log ratios was generated, which was then used for further analysis. The data were then loaded into BRB ArrayTools (Simon et al., Cancer Informatics 2: 11-17 (2007)). To obtain a single expression ratio value for each unique probe on the array, a mean ratio value was calculated for all probes present more than once. Alternatively, expression data was loaded and analyzed in R/Bioconductor software.

Prognostic Gene Selection

Unsupervised hierarchical clustering based on full-genome gene expression measurement indicated the existence of 3 main colon molecular subclasses (see FIG. 1). Survival analysis of the three 3 classes showed that one subtype had a relative poor outcome (subtype C) and one subtype (subtype A) showed a good outcome (5-year distant metastasis free survival Hazard ratio A vs. C of 1.8, P=0.15). Further investigation of these subtypes indicated that both survival-associated subtypes, A and C, were enriched for samples with an activating BRAF mutation status (BRAFmut), especially for the good-outcome class (good-outcome class A: 52% BRAFmut, poor-outcome class C: 22% BRAFmut, compared to 4% for remaining subclass B). These finding suggested that samples within classes A and C showed a different gene expression pattern which is likely linked to the activated BRAF mutation phenotype. The BRAFmut subclasses were apparently enriched for colon samples with micro-satellite instability (MSI). The observed colon clustering might therefore represent the two known different colon tumor development pathways: MSS (subtype B) and MSI-derived (subtype A and perhaps also subtype C).

As cluster A and C can be discriminated based on full-genome unsupervised clustering, the differences between BRAFmut samples with a good and poor outcome are relative large. This large difference within BRAFmut samples might mask more general prognosis-related gene expression that is apparent for all colon subtypes, including subtype B, which consists for 96% (100/104) of wildtype BRAF samples with a mixed prognosis outcome. To circumvent the strong BRAFmut related gene expression differences, prognosis related gene expression was further investigated within subtype B samples only (n=104) and subsequently applied to all samples (n=188).

Using the "leave-one-out" cross validation procedure, all genes were scored for their association with 5-year distant metastasis free survival (DMFS). A set of 209 genes showed robust DMFS association in at least one iteration (Table 1), while 38 non-redundant probes (from a total set of 44 probes) showed robust DMFS association over 50% of all iterations (see FIG. 2).

To ensure that the selected genes are optimally suited for diagnostic use and will result in equal readouts using a different array type and/or reference, we confirmed the expression measured on HD against the CRP reference to that on a different low-density (LD) array type and using a different reference (universal human cell line, UHR). Eighteen of the 38 probes could be matched to the LD and showed a highly correlative gene expression readout (R2>0.50) across 128 training samples that have been analyzed using both platforms. These 18 probes, corresponding to 18 genes or ORFs, were used for subsequent profile development (see FIG. 7).

Example 2

Classifier Training

The 18 identified genes were used to construct a colon prognosis classifier that is analogous to a previous defined, breast cancer prognosis signature (WO2002103320; which is hereby incorporated by reference). For each sample, a low-risk score and a high-risk score was calculated based on the 18-gene expression pattern in that sample. Both scores were combined into a final index. The optimal threshold for the classifier index score was determined in such a way to reach optimal sensitivity and specificity. If a sample's index exceeded a threshold (−0.05) it was considered as a high-risk samples, and visa versa. Survival analysis of the profile outcome on the training cohort (using a Leave One Out cross validation procedure) indicated a hazard ratio (HR) of 3.41 (P=1.4e-5) with a 5-year DMFS rate of 82% (95CI, 76-89%) for low-risk samples and 50% (95% CI, 38-66%) of high-risk samples. Disease-free survival is relative low for both high- and low-risk classes, likely because the great majority of samples within the training cohort did not receive adjuvant chemotherapy. Analysis separately for BRAF wildtype and BRAFmut samples confirmed that the 18-gene profile is independent from BRAF mutation status (FIG. 3).

Example 3

Classifier Evaluation

The 18-gene profile was validated on an independent cohort of 178 stage II and III colon samples. The profile classified 61% of the validation samples as low-risk and 39% as high-risk. The low- and high-risk samples showed a significant difference in DMFS with a HR of 3.19 (P=8.5e-4). Five-year DMFS rates were 89% (95CI, 93-95%) for low-risk and 62% (95CI, 50-77%) for high-risk samples.

In the sub-analysis of stage II patients only, the 18-gene profile had an HR of 3.61 (0=0.01)—Five-year DMFS rates were 91% (95CI, 84-98%) for low-risk and 71.8% (95CI, 57-87%) for high-risk patients. In the sub-analysis of stage III patients only, the 18-gene profile had an of 2.72 (0=0.045)—Five-year DMFS rates were 84.3% (95CI, 71.4-97.2%) for low-risk and 49.4% (95CI, 27.4-71.3%) for high-risk patients.

Next, we investigated whether the 18-gene profile showed prognostic power for samples from untreated patients only, or also for patients treated with chemotherapy. The 18-gene profile showed a significant performance for both untreated samples (P=0.0082), and treated patients (P=0.016) indicating that the performance of the profile is not caused due to treatment benefits (FIG. 5).

It was found that patients with MSI-H had a high frequency of B-Raf mutation (50%) and were mainly the 18-gene profile low risk (19/22=86%) indicating that the good prognosis of the MSI-H patients is identified by the gene classifier.

For comparison of the classifier to other clinical factors, only results from the Validation Set were used. In the univariate analysis, the 18-gene profile was the strongest predictor of DMFS. Only stage and lymph nodes status showed a similar magnitude of statistical significance. In the multivariate analysis of all samples, or of only stage II or stage III patients, the 18-gene profile remained the strongest significant independent prognostic factor (Table 2). For the multivariate analysis, all clinical parameters with a p-value of 0.1 or better in the univariate analysis were included.

When results from the 18-gene profile were compared to the currently used risk assessment based on the ASCO recommendation (referred to as ASCO risk), the 18-gene profile outperformed the clinical risk assessment (Table 3). The multivariate analysis for the stage II patients shows that the gene expression profile is the strongest predictor for developing distant metastases independently from the factors listed in the ASCO recommendation analysed either alone (HR=3.56, 95% CI 1.35-9.39, p=0.010) or combined (HR=3.6452, 95% CI 1.3337-9.3365, p=0.011). There is a high degree of discordance in risk stratification between the 18-gene profile and ASCO criteria indicating that the 18-gene profile can complement and improve the clinical risk assessment.

In the stage II patient sub-group, amongst 41 patients (36%) who received adjuvant chemotherapy, 28 (68%) were classified as low-risk index and 13 (32%) as high-risk by the 18-gene profile index, and chemotherapy administration was not a significant prognostic factor either.

Example 4

Treatment Benefit on Low-Risk and High-Risk Patients within Validation Cohort

A treatment benefit of chemotherapy was determined by analysis of the 5-year DM development rates of treated vs. untreated 18-gene low-risk and high-risk patients. Treatment benefit was absent from patients classified as low-risk (stage II/III, −0% DM; stage II, +2.7% DM). Treatment benefit on high-risk patients was observed (stage II/III, −10.4% DM; stage 11, −9.5% DM). These results (FIG. 6) indicate that high-risk patients are more likely to benefit from chemotherapy.

Example 5

MCTP1/THNSL2 Ratio for Colon Prognosis

The prognostic power of a two-gene prognosis model was exemplified using MCTP1 and THNSL2 genes. A threshold for the MCTP1/THNSLC2 ratio was determined on the 188 training samples and showed a significant performance with a HR of 3.1 (P=6.8e-5). Samples with a high MCTP1/THNSLC2 ratio above the threshold were classified as low-risk. The MCTP1/THNSLC2 ratio model was confirmed on 178 independent validation samples and showed a significant HR of 2.3 (P=0.017) (FIG. 8). Validation samples with a high MCTP1/THNSLC2 ratio (low-risk) showed a 5-year DMFS of 87% (95CI, 80-95%) and samples with a low MCTP1/THNSLC2 ratio (high-risk) showed a DMFS of 70% (95CI, 60-82%).

Example 6

Additionally, we investigated the 18-gene profile on a cohort of 30 stage I colon cancer patients. One patient showed development of distant metastasis. This patient was correctly identified as high-risk by the 18-gene profile (FIG. 9).

TABLE 1

| 18-set | 38/4-set | Sequence | Gene Name | Systematic Name | SEQ ID NO |
|---|---|---|---|---|---|
| y | y | TTAGAAGAGATGGCTTATTAACAGGGAAGAAGCTTGTTATATTCCAGTTGTAAGAATAGC | ZBED4 | NM_014838 | 1 |
| y | y | CATTTCCCTGCAGATGGTACAGATGTTCCTGCCTTAGAGTCATCTCTAGTTCCCCACCTC | LIF | NM_002309 | 2 |
|  | y | GGGAGCCTTCTTGATGATCTCAAAAATAATAGCTATTCAAGAAAATCACCAAGTGACTGT | IL18R1 | NM_003855 | 3 |
| y | y | AGCCTGAGCGTTTAATTTATTCAGTACCTGTGTTTGTGTGAATGCGGTGTGTGCAGGCAT | PIM3 | NM_001001852 | 4 |

TABLE 1-continued

| 18-<br>set4-set | 38/4<br>Sequence | Gene Name | Systematic<br>Name | SEQ<br>ID<br>NO |
|---|---|---|---|---|
| | TTTTGAAGAAAAAGTCCTTCACTTTTCCAAGAGACCATACGTCAGTTAC<br>AACTAATACAG | PYROXD1 | NM_024854 | 5 |
| | TCCATATCTTTGTTTTAACCAGTACTTCTAAGAGCATAGAACTCAAATG<br>CTGGGGGAGGT | PPARA | L02932 | 6 |
| y y | AGAGAGGTTTCCGCAGAATAAAAAGCGGGTCACTCTATATGCTCTGTAC<br>AGGAAACTCTA | IL2RA | NM_000417 | 7 |
| y y | TTTTGAAGAAAAAGTCCTTCACTTTTCCAAGAGACCATACGTCAGTTAC<br>AACTAATACAG | PYROXD1 | NM_024854 | 8 |
| y y | AGTCGAAAAATCCCAAGGCCCAAACCTGCACCACTGACTGCTGAAATAC<br>AGCAAAGATT | CTSC | NM_001814 | 9 |
| y y | ATTACCACCTGTAATTCCTCTTTGGATTGTGTAGACTCAACATGAGACA<br>TTCCTTTCTGC | EDEM1 | NM_014674 | 10 |
| y y | TCTCTATAATGCAGCTGTGCTCTGGAGTCCTCAACCCGGGGCTCATTTC<br>AAACTTATTTT | M6PRBP1 | NM_005817 | 11 |
| y y | GGAAGTGACAACTGAACACACTGTGTTGGATCGGAGGTTCCGTTAGGGG<br>ATCCTTCCTTA | SLC6A12 | NM_003044 | 12 |
| y y | ACCCTGATGCGGAGAGGTGACAACTGGATGCTGATGCTTCGGGACACCA<br>TTGAGGACCTT | THNSL2 | NM_018271 | 13 |
| | y | AGGGACCTAGTGAAATCAATGAAACTCTTGAGTCTTGCTTAGGCTCGCA<br>AACAAGAAGTG | KCNJ10 | NM_002241 | 14 |
| | y | AACAGAGGGCAGAAGGTCTATACGTCCTGAGGCCTTTTATGCAACGTTT<br>GTTTGTGGAAT | THC2663361 | THC2663361 | 15 |
| | y | TGAAAAGCATTATCAACAGAATGAGGATAAGATGAGAAAATCCTTCAAT<br>CAGCAGTTAGC | C10orf67 | NM_153714 | 16 |
| | y | TGAAAATGAAAAGTCTTGATGTAGTCAGATGGTTACTCTCTTAACATTA<br>GGTATTACCCC | KIAA0040 | XR_041165 | 17 |
| | | ACCCTGATGCGGAGAGGTGACAACTGGATGCTGATGCTTCGGGACACCA<br>TTGAGGACCTT | THNSL2 | NM_018271 | 18 |
| | y | AGAGGCCTTGAATACTCAGAAAATGGGAGATTGTGAATGGGTGTAGAGG<br>ATATCTATGAA | BC040628 | BC040628 | 19 |
| | y | AAGGAAAATGAATACTGTGTAATAGTTAAACCCATTCATAGGTTGCAAT<br>AGAGTGTCAGC | AK096685 | AK096685 | 20 |
| | | GAAGCTTTTGTCAGTAACCTCAATGGAACCACCGTGCTGGAAATCACCC<br>AGGGATTGTGC | PIGW | NM_178517 | 21 |
| | | AGCCTGAGCGTTTAATTTATTCAGTACCTGTGTTTGTGTGAATGCGGTG<br>TGTGCAGGCAT | PIM3 | NM_001001852 | 22 |
| y y | ACGGTTATTGACCCCATAGACTAGGGTAAGAATAAAGGCAATAAATTTG<br>GTCTGACTCAG | PPARA | NM_005036 | 23 |
| | y | CCAAAACGCCATTGCCTTCCGCAGAGACCAGAGATCTCTGTACTTCAAG<br>GACAGCCTTGG | COLQ | NM_080538 | 24 |
| | y | AAGAACTACCGGAGACAAGAAAGGGACACTCTCTAGAGAAGGCTTCAA<br>GGAAAGCTTAT | AK021427 | AK021427 | 25 |
| | y | TCTCATTCCAGCATGAGCGTTTCTGAGTCTCTTCAAGACGAATCTAGTT<br>TTCACCTTCAC | C15orf27 | NM_152335 | 26 |
| | y | AGATCTTTGTAGGTTTAGACATGGCTCCCTGTCTCCAGTAAACATCCAG<br>CCATTCAGACA | PRDM4 | NM_012406 | 27 |
| | y | AGTTCCAGATGTACATGGTATATTTTGAAGTAGAAATAAAAGAATTACT<br>TATTTTTCTAA | LOC165186 | NM_199280 | 28 |
| | | CTCCATCTTATTTTCATGTATATGTGTTCATTAAAGCATGAATGGTATG<br>GAACTCTCTCC | IL2RA | NM_000417 | 29 |

TABLE 1-continued

| 18-38/4 set | 4-set | Sequence | Gene Name | Systematic Name | SEQ ID NO |
|---|---|---|---|---|---|
| y | y | AACCTGGAGCAATTTAAATAGGCTAAATGGTTTTGATTAAATCTTGAGC TCCGAGTTGGA | ZNF697 | NM_001080470 | 30 |
|  | y | ACTGATGACTGCGCCTGTGTTCCAGAACTGTTCCGTCTCCCTGAGATCT ATTCCCTCCAC | CRYGA | NM_014617 | 31 |
|  | y | GAAATGTTCAGCAGATTTTGGTTTTGAATTTTCTTTCATCAGTATCACC CATATGAGCAG | EEPD1 | AF161370 | 32 |
| y | y | TCTAATTTTGAATTCTGACCATGGATACCCATCACTTTGGCATTCAGTG CTACATGTGTA | LAMA3 | NM_198129 | 33 |
|  | y | CAATACCCATCTCGTGTATTAATCCCATCAATCATTCAGGTGTCTGGAA TACAATTCTTT | NEDD8 | AK125214 | 34 |
| y | y | TGATCTTTCACTTGTTAACTAGGGAAAAACACTAGTCACCAGTGTGGTA CAAACTTGTAC | CA438802 | CA438802 | 35 |
| y | y | TGTGTGGTAGAACTGAACAACGATAGACTGCTAACACATACTGTCTACA AAAATCTCAAT | MCTP1 | NM_024717 | 36 |
| y | y | AAGTCCAAGACTCAGTGATCGAAGGATGACAGAGATGTGCAGTGGGTAT TGTTAGGAGAT | HSD3B1 | NM_000862 | 37 |
| y | y | ACATTACCTTCAGGAGACTTGATCCCAGTAGACTGAGGTCTTCCCTTTC AGCAGAAAGAT | CYFIP2 | NM_001037332 | 38 |
| y | y | TTGAGGTTGTCTGAGTCTTGGGTCTATGCCTTGAAAAAGCTGAATTAT TGGACAGTCTC | IL2RB | NM_000878 | 39 |
|  |  | CATTGTCAGTGCTACAGGAGTTACACCAAATGTAGAACCTTTTCTCCAT GGTAACAGTTT | PYROXD1 | NM_024854 | 40 |
|  | y | CAGAGGTGGGGCCATAGAATCCTACACTACAGCTTTCAGTTTTTTAGAA AATGTGATAAT | XKR3 | NM_175878 | 41 |
|  | y | CAGCCTTTCCTCATGTCAACACAGTTCACAATATAGTTTTCAAAGTACA GTTTAAAACTC | NT_035113.6 | NT_035113.6 | 42 |
|  | y | TGGGAGAGCGTTGGTGGATGTGTTCTGCATGTTCCTTTCTGTACAGTAA CTTCTGCATTT | THC2520461 | THC2520461 | 43 |
|  | y | TTGCTTTGAAAAGCTTCCTCCAAAAGCTGTATTGTGGTACTTTTGACTC TGGGACAAGAG | THC2662025 | THC2662025 | 44 |
|  |  | CACAGATGTTTTTCAAGTTCCTCAGTTTGTACTGAAATTAGGGATTCAT CAGGGCAGGAA | LL22NC03-5H6.5 | NM_017931 | 45 |
|  |  | GTAATGCCTGGCCGCAGTGTGTGTGTATCCCATACCCCACTCTGGAAGG AACCATCCAGT | POLR2L | NM_021128 | 46 |
|  |  | CATTGTCAGTGCTACAGGAGTTACACCAAATGTAGAACCTTTTCTCCAT GGTAACAGTTT | PYROXD1 | NM_024854 | 47 |
|  |  | AACAGTTAACAGGATGCAGACATGGCAGAGGTTTCCTAAAAATCTCATT ATCTATAACCA | MGC5370 | BC0006795 | 48 |
|  |  | CCAGGGTTGTAGCCCTGGATACTATCGGGATCATAAAGGCTTGTATACC GGACGGTGTGT | LAMA3 | NM_000227 | 49 |
|  |  | ATACATTTAATTCCTCACGTTTTATATTGGAGAGTTCGGTACAGACTG TCCATTACTGC | THC2650457 | THC2650457 | 50 |
|  |  | TTTAAATCTCCACAGACGTATATGGATGGTTACTGCATTATGTATCTG TAATAAGCGAC | LAMA3 | NM_198129 | 51 |
|  |  | TTCGTCACCTGTAGAGCGTTTGTCACTGTTCATCTGGTATTAAAGATTC CACATTCTCAT | LOC645195 | AK123450 | 52 |
|  |  | CCCCACAGGCCATGACCTTGAAGTGAAAGTCTTCTGTTGCTATTGTGGG CTCAAATATTT | RNF141 | NM_016422 | 53 |
|  |  | GTGAGTTCATGGAAGTCTAAATCAGTAATTTAGAGGATAGTGACACTCA ATCAGTTTGTA | RP4-692D3.1 | AK024625 | 54 |

TABLE 1-continued

| 18-38/4 set4-setSequence | Gene Name | Systematic Name | SEQ ID NO |
|---|---|---|---|
| TGCAGAGAGAATGTCTTCATAGAGAGAATGTCATTAAATACTTGAATCTGCATGACAGTT | PSD3 | NM_015310 | 55 |
| TAGATGAATGGATTATCTGCACTGATTGGGATGTCGGTTTTAGAGAGGGTCAACAGTATG | ENST00000302942 | ENST00000302942 | 56 |
| ATCTTAGAAACACCTTGAAGTATGCCAAGAAAAACGTCCGTGCATTTTGGAAACTCAGAG | APOL6 | NM_030641 | 57 |
| AGATTACATTAATTTTTCTATAAATTGGAAGATTTATAAATGTTTGAAATTGTACACATT | GK | NM_203391 | 58 |
| CAGTGGAACTGATGGACACAAGCTTATCGCCACACTGGTTTTCCTCTGAAACAAGGCCCT | MGC23270 | BC015579 | 59 |
| CCTGGATAACCTGAGGCGAGTCATGCCATGCTACTCTAAAACCCAAAAACTTTCCAAGAT | NEUROD4 | NM_021191 | 60 |
| ATGTAACTGATTTTCTGCTAGAAGTTTGATATCCTCTGAATTTAGCTAAAGGATCACCAG | SQSTM1 | U46752 | 61 |
| CAAGTTTTCCTTGCTTTCCTGATACTCTTTGGCGCTGACTTGGAATTCTAAGAGCCTTGG | RAD9A | NM_004584 | 62 |
| CATATTCCATTTTTAAGAAGAGGTGTTCCAGTTCTGCATCTGATACCGTCTCCTTTCCCT | QPCT | NM_012413 | 63 |
| TGATCGAGAAGCTGCTCAATTATGCACCCCTGGAGAAGTGACCACGCTGAAACCCACCCA | POLR2L | NM_021128 | 64 |
| TTGAGGTTGTCTGAGTCTTGGGTCTATGCCTTGAAAAAGCTGAATTATTGGACAGTCTC | IL2RB | NM_000878 | 65 |
| TTCTTGCCCTAAACAAGCAAAGAAAATGCAGAGGTCTCATCCTTAAGACTCAGAAGCTAA | THC2677796 | THC2677796 | 66 |
| CAGACTCTCCACATGTGCTCTACTAGTGAGTGCCTTATACTCTCAGTATTTTGGGGCTTA | PPARA | NM_005036 | 67 |
| CAGCCTTTCCTCATGTCAACACAGTTCACAATATAGTTTTCAAAGTACAGTTTAAAACTC | NT_035113,6 | NT_035113.6 | 68 |
| GCAATGAGTGAACTGACTGTGGCTACATTCTTGAAGATATACGGGAGAGACGTATTATTA | CD521938 | CD521938 | 69 |
| AACAGTTAACAGGATGCAGACATGGCAGAGGTTTCCTAAAAATCTCATTATCTATAACCA | MGC5370 | BC006795 | 70 |
| CCAAATTTATGTGGTTGTTACACTTCCATAGTTGTCTTAGCCGAATCCTTCCATATTCTT | CCBL2 | NM_019610 | 71 |
| TTCCAGATGAGCTCTTCTTTCCTACAAGTTTTCATAATTAGGGAATGCCAGGGTTTAGGG | RNF41 | NM_194358 | 72 |
| GTAATATGTGAAGATTAATGGCAATGAAGCAAACGTGCATAAGAAAATCCACGCAGCAAA | LOC100133746 | AK097452 | 73 |
| GCAAACTTGGCAGTCATAAACCCACATCTACTCTAACAAGTCTGAATGGTGCATAAGTAC | WTAP | NM_004906.3 | 74 |
| TTGGTTGTGAGATCCAGAATAACAGAAGCACTGGAGCATTCTGGAAGAATGCCTATGATG | LOC646282 | XR_017216 | 75 |
| CTTCTGTTAGCTCTGGACTCTTAACACTTAAGTTACTCTTCTGAAATTGCTAGGACCATT | RBM4B | NM_031492 | 76 |
| TGTACCTACTGATGGTGCTGTAACCACCTCACAGATTCCAGCTTCGGAACAAGAGACCCT | MDM2 | NM_006879 | 77 |
| TTTGATGTAGCTCTACCGATACTATGTGGTAATGCTATTTTGTTTTACTAACAAGCTCTG | U68494 | U68494 | 78 |
| CACTCCCTTGGAAAACAGTAAACATCATTTTGGAATGTGAACAACCAGAGACTACACAGG | CTSC | NM_148170 | 79 |

TABLE 1-continued

| 18-38/4 set4-setSequence | Gene Name | Systematic Name | SEQ ID NO |
|---|---|---|---|
| ATCTTAGAAACACCTTGAAGTATGCCAAGAAAAACGTCCGTGCATTTTG GAAACTCAGAG | APOL6 | NM_030641 | 80 |
| TCCTGACAAGTTTTTCTCCCATGTCCGAGATGGCCTTAATTTTGGTACA CAGATTGGCTT | C13orf31 | NM_153218 | 81 |
| AGTGACTCATTTACCAACATTAAACCCTAGGATAGATGCAACAGAGAAG TACTACTTCCT | AK056973 | AK056973 | 82 |
| TGAGCAGCTTGTGAATGTAACTGATGATCTACTCATATATAAGATCAGA TTGGAAAAAGC | TEKT1 | NM_053285 | 83 |
| GTTCGAGAGCCGAGTCTGTGGGCACTCTCTGCCTTCATGCACCTGTCCT TTCTAACACGT | CD81 | NM_004356 | 84 |
| AAGCTGTGCCTCGACACATCCTCATCCCAAGCATGGGACACCTCAAGAT GAATAATAATT | ICOS | NM_012092 | 85 |
| AATATTTGTGTAACGGAGATATACTACTGTAAGTTTTGTACTGTACTGG CTGAAAGTCTG | IKZF4 | NM_022465 | 86 |
| GCCTTTAGTTCTCCACTGGGGAGGAATCCTGGACCAAGCACAAAAACTT AACAAAAGTGA | LAMB3 | NM_001017402 | 87 |
| TTTGTGAAATAATGTACCATAGACTCTCACCAACTGTATATACCTGTAC ATATCAGAAGC | DEPDC5 | NM_014662 | 88 |
| AAGGTTCCATGGTAGCTAAGTGTGGACAAGCTAATCACTGAAGTTCCCT GATGCAGAGTT | BC030122 | BC030122 | 89 |
| TATGTACAGTTTACATGAATGTTCCTCAGGACATGGCATACAATGGCCT TGGAGGTCCAA | APOL6 | NM_030641 | 90 |
| TATTGTAAACTTTGTGGCTTTTGGTCTGTGATGCTTGGTCTCAAAGGAA AAAATAAGATG | C8orf4 | NM_020130 | 91 |
| ACATTAACCAGCTCCTGAGAACCATGTCTATGCCCAAAGGTAGAGTTCT GGATAAAAACC | GPC3 | NM_004484 | 92 |
| TGAACATGGAGGATGACCAGAACTGGTACAAGGCCGAGCTCCGGGGTGT CGAGGGATTTA | GRAP | NM_006613 | 93 |
| CAACACCATCCTCATCTGCATGGTGATCCTGCTGAACATCGGCCTGGCC ATCCTCTTTGT | JPH2 | NM_020433 | 94 |
| GTGTGGAAACATCTATCCTATAGATCATCCTATTCTTATGTGTCTTTGG TTATCAGATCA | QPCT | NM_012413 | 95 |
| AGTTTCCTATGTTTCACTGTGCAAATATATCTGCTATTCTCCATACTCT GTAACAGTTGC | CYP2C9 | NM_000771 | 96 |
| GAAGGACAATGTCTGAATTAAATGCCGTGCTTTAAACTGAAAGGGAAAC TTAGCAAATAA | NT_026437.11 | NT_026437.11 | 97 |
| ATACAAAGTGCAAAAAAGCTTGGCTCCTTCTGTATTCTTTAAAAACAAA ACAACAACAAA | CR622844 | CR622844 | 98 |
| CAAGCTTCCTTCTTTCTAACCCCCAGACTTTGGCCTCTGAGTGAAATGT CTCTCTTTGCC | PAX8 | NM_003466 | 99 |
| AGACAATGGGAAAGTAAGTTATAAAAAATACTGGGAAATCTGTTTCTCT TCTGAGCAAGC | C6orf105 | NM_032744 | 100 |
| CGCAGCCTTCGGTATCCCCTGCACAGATAAGTTTGTCGTCTTTTCACAG ATTGAGATATT | IL3RA | NM_002183 | 101 |
| AAATGCCATGCGGTTTTTCAACTTCTCATGGAGGGTCACTGCCGATCAG CTCAGGAAAGC | ECE1 | NM_001397 | 102 |
| AACAACGGGTTTCTGTTCCAACTGGTTGATCAACTTCTTGAGTCAACAA GTCCCAAAACC | BC053669 | BC053669 | 103 |
| GATGGATCCACTGGAGGTTAAGACATGTGGTAAGACAGTGTAATAGGAA GCTGCTCAGTT | HLA-DMB | BC035650 | 104 |

TABLE 1-continued

| 18-38/4 set4-setSequence | Gene Name | Systematic Name | SEQ ID NO |
|---|---|---|---|
| GTGGGGAGGGTTTCTTGGGTTTCTTGAAGCCAGTATTTCCCATAGTATC TTACGTCCCAG | C20orf200 | NM_152757 | 105 |
| TAAACAGTAAAATAAGTACTCATCCGATAAATTCAAAGTAATTTTAGAA CATTTTGACCA | AF090895 | AF090895 | 106 |
| ACAGCTCTAGAAATCCTTATGCCATTTGCAACTACATACCTTTGTGAGT TGGGATTTTCA | LOC63920 | NM_022090 | 107 |
| ACACTAAAAGTTGCTTCTAATAGGTGGCATATGTCTCTGCTGTGAATGA CATGACCTTAC | LOC642032 | BC035659 | 108 |
| CTGATGGATGAGAAGTTTACATGCAATGATTTCTAGTAGCAGGTTCGTA TAATTTTTCAC | LOC400620 | BC014643 | 109 |
| CGGCCTCCGCGGTGGACGTGTTCTTTTCTAAGCCATGGAGTGAGTGAGC AGGTGTGAAAT | CHID1 | NM_023947 | 110 |
| AGTTACAGAAGCCTGGGTAACTGCAGCTTCTTCACAGAGACTGGTTAGC AACCAGAGGCA | VSTM3 | NM_173799 | 111 |
| GCCAAAGGTTAAGACAATTGAACTTGAAGGAGGTCTTTTGGAAGATCAC TTTGAAACTAC | ERAP2 | NM_022350 | 112 |
| GGTATTTTGAAGTACTGGGCTTATATTTAATTGGAATACATGTGTACAG CAATAAGCAGG | PLEKHA5 | NM_019012 | 113 |
| CTGAGCCCAAAACTCAAAGCCAAACCTGTCAGCTCTCTGAATGAGTGCA CGACCAAGGAT | SPTBN5 | NM_016642 | 114 |
| AAAGCTTGGTGTTTTCTCTGGGTACACCCCAAGCAGCGTCTCCTTTTGG ATACAGTTATT | RHOH | NM_004310 | 115 |
| ATCTTTATCTATGATGCTTTCAAGAAGATGATCAAGCTTGCAGATTACT ACCCCATCAAC | SLC4A4 | NM_003759 | 116 |
| AGTCACAGTTACCGCGTGTACTACAATGCCGGCCCCAAGGATGAGGACC AGGACTACATC | SCO2 | NM_005138 | 117 |
| TGTGAGATGTTCCCCCTGCTGTAAATGCAGGTCTCTTGGTATTTATTGA GCTTTGTGGGA | IER3 | NM_003897 | 118 |
| AAACTCAAAGAGAAGGAGGGAGATCCGGTGTCCTTATTACATACAAGAC TCAGGAACCCA | CSF2RA | NM_172249 | 119 |
| CCTAGCTGGACTCATGGTTCCTAAATAACCACGCTCAGAAGCTCTGCTA GGACTTACCCC | FGD3 | NM_033086 | 120 |
| TATTGTTAAGTTTCTGTTGACGGGTTAGAGAGCACGGGTTTGGCTGTGT GCTGGTTATTC | THC2746246 | THC2746246 | 121 |
| CAAAAGCAAGTCATGGCTAGAGTATCCATGCAAGGTGTCTTGTTGCATG GAAGGGATAGT | TXNRD1 | NM_003330 | 122 |
| GAGATGCCTGTGTAATTTCGTCCGAAGCTGCCAGGAAGAAGAACAGAAC TTTGTGTGTTT | IL3RA | NM_002183 | 123 |
| AAAGAGGAATCGGGAAACCCTGGGTAAAAGTCGTCCAAGTGGAACTTCC TTTGGTCGGGG | THC2515921 | THC2515921 | 124 |
| AAAGGAAACGCGACGAAGAACTTGCCAAATCTATGGCCATATCCTTGTC TAAAATGTATA | OTUD1 | AB188491 | 125 |
| CAAAGATGCATTTACCTCTGTATCAACTCAGGAAATCTCATAAGCTGGT ACCACTCAGGA | GBP1 | NM_002053 | 126 |
| CTGCCCCGGATGTGGCCGAGGGGCTTCACCCTGTGTCCTTAGGAGGGGG TGGCCTTGAGG | BRF1 | NM_145685 | 127 |
| GGCTGAACTACAAGTGTAGGCCACCATTATAATTTATAAATACAGCATA CTTCAAAACTG | RHOU | NM_021205 | 128 |
| CCGTCTCTCTGCACAGCACAGAAATTCTCAATCACTGAAATGAGTAACT GCAAAATAAAT | MPPE1 | NM_023075 | 129 |

TABLE 1-continued

| 18-38/4 set 4-set Sequence | Gene Name | Systematic Name | SEQ ID NO |
|---|---|---|---|
| GGTCTTGGTAGAAGCGCGTGCAAAAGCCATTCTGGACTTCCTGGATGCC CTGCTAGAGCT | GSDML | NM_001042471 | 130 |
| AGAACTGGAAGCTTGGAGGAAAGCATACTGGAGAATAAGCTACAAAGAG CCTGGGCTTAA | CCDC142 | NM_032779 | 131 |
| AGAAGTGGAACCGCTTACTACAGAAGGGATGGGTTGACTTTTTTGTTCC AAAGTTTTCCA | SERPINA7 | NM_000354 | 132 |
| GACTGTGGAATGGAATGACTCTCCAGAGCTGCAGATTGAAGGCATATTT TCATCTGACTT | LOC387895 | BC040060 | 133 |
| TGCTTTTGTCATAGTTCCACTCTCTCAGATACATGTATCTAATGAAACT GAATAAATCCG | TAGAP | NM_138810 | 134 |
| GACCCAGTCACACCATCCATGAAAAGCTGTTTCTATAATATGAAAAATT GTTAAATGACG | AF143325 | AF143325 | 135 |
| ATTACCCTATTTCACTGTTGTTCAAGTAAATCTAAACCTTGTAGACAAG TGAGTCATCTG | PSD3 | NM_015310 | 136 |
| TCACGCCCACACCAGATGATGCTGTGTTTCGCTGGCTCAGCACTGTCTA TGCTGGCAGTA | CPXM1 | NM_019609 | 137 |
| ACCATGTGGAGATGTTTCTGGACTTGCTAGAGCCTGCTTAGCTGCATGT TTTGTAGTTAC | LMAN2L | NM_030805 | 138 |
| TGAAGACAGTCCCTATCCTAGAGGGGTTGAGCTTTCTTCCTCCTTGGGT TGGAGGAGACC | SLC43A1 | NM_003627 | 139 |
| TTGGAGAATGTGTAATTAGAGAACTATAAGATAAAGAGATAATCTTTAG AATTTGAATGT | BC034791 | BC034791 | 140 |
| GAAGACACTCCAGAAAATACAGAAACTGCATCTGTGTGCACCAAGGTCT GAAAAATGACT | SLC23A1 | NM_152685 | 141 |
| GGTCTTGGTAGAAGCGCGTGCAAAAGCCATTCTGGACTTCCTGGATGCC CTGCTAGAGCT | GSDML | NM_018530 | 142 |
| CAGCCTTTCCTCATGTCAACACAGTTCACAATATAGTTTTCAAAGTACA GTTTAAAACTC | NT_035113 | NT_035113 | 143 |
| TTTGTGTATCAAGTCCCACTATCAAGGATAAGCCAGTCCAGATTCGGCC TTGGAATCTCA | CPEB4 | NM_030627 | 144 |
| GAAGACACTCCAGAAAATACAGAAACTGCATCTGTGTGCACCAAGGTCT GAAAAATGACT | SLC23A1 | NM_152685 | 145 |
| AAGAACGAAAGAATAGTTAGGATACCAATGAGTAAAAGGGTTCCTGTTC ACTCTGACTCT | EFHD1 | NM_025202 | 146 |
| GGCCATACGCCATGCCATAGCTTGTGCTATCTGTAAATATGAGACTTGT AAAGAACTGCC | TAGAP | NM_054114 | 147 |
| CTGCCCTGTGTTCGTGGTGCAGTGGCTGTTTGACGAGGCACAGCTGACG GTGGACAACGT | NOTUM | NM_178493 | 148 |
| GCTCAGGGAAGGGGCTGGGATCGGAACTTCCTGCTCTTGTTTCTGGACA ACTTTCCCCTT | KLHDC7B | NM_138433 | 149 |
| CTTTAGACCTTTGTCCCCGTCACTGCCAGCGCTTGGGCTGAAGGAAGCT CCAGACTCAAT | FXYD2 | NM_021603 | 150 |
| CCCAGTGGAAAATCGCTTATATACCTATGACCACACAACCATCCTGGCC GTGGTGGCTGT | HBEGF | NM_001945 | 151 |
| TTTTGATGAGAATGAATCTTGGTACTTAGATGACAACATCAAAACATAC TCTGATCACCC | CP | NM_000096 | 152 |
| GCAAAGCCTTCAAAATGTATCGTGCTTGAATTTTGACTCTTCTGAAATA GAATAACTGAC | NUP50 | NM_153645 | 153 |
| AGGATTTCAAGGAAGTGTTTGCTATTCAGGAAACAAATGGGAACAGTTG ACTGGTTTAGT | LOC93349 | NM_138402 | 154 |

TABLE 1-continued

| 18-38/4 set4-setSequence | Gene Name | Systematic Name | SEQ ID NO |
|---|---|---|---|
| CTTGGTTCATCTATTTTCATTAAACCATAGTCTTTGTCTGCTGGATGATACGTCGCCAAG | THC2478115 | THC2478115 | 155 |
| CCAAAACAGACATGAGCCCACTGCTTGGAACAACAAACTGTCCTGGTTGCTGGTCAGAGG | HSD17B1 | BC019592 | 156 |
| GGTCTTGGTAGAAGCGCGTGCAAAAGCCATTCTGGACTTCCTGGATGCCCTGCTAGAGCT | GSDML | NM_018530.2 | 157 |
| GGCAGCAGGAAGCGGAGTCGAGACCACTTCCGGAACAAGAGCAGCAGCCCCGAGGACCCA | TSSC4 | NM_005706 | 158 |
| CGGAAGTCCTGATGTATAGCAAGTTCAGCAGCAAATCTGACATTTGGGCTTTTGGGGTTT | BTK | NM_000061 | 159 |
| AGAACATTGTACCATGCCTCTTCTGTATCTGTGGAAGTTTCCTGTTTGACACAGGGTATC | HMG2L1 | NM_005487 | 160 |
| TCAGAAGGCTCTTCTGACTACTGGGCAAAGAGTGTAGATCAGAGCAGCAGTGAAAACAAT | CXCR6 | NM_006564 | 161 |
| ACTAGGAAGTATATGCCCCCAAATTATGAAATTCCATTTCAAACAGAATTAACAGAATTT | ENST00000360738 | ENST00000360738 | 162 |
| TTTGGGGATTTTGTTTTCCCTTGGTCTAATGGAGAGAAAGACATTTTGGTTTTCTTTTTC | MYT1 | NM_004535 | 163 |
| GGTTTATTGACATGGAATGATTTGACCAAGGTGATATAGTGGTTAAGCAGTTAAGTGATT | THC2699065 | THC2699065 | 164 |
| CTGAGATGCTGATGTCATGGAGAGTAAACGACCACAAGTTTACCCCACTTCTCTGTGAAA | NR1H4 | NM_005123 | 165 |
| TCCAGATGTAAACCCCAAACTTGTACACAAAAGAAAGCACAGATTGTTTACCTGTTGTGG | FHOD3 | NM_025135 | 166 |
| CTTTAGACCTTTGTCCCCGTCACTGCCAGCGCTTGGGCTGAAGGAAGCTCCAGACTCAAT | FXYD2 | NM_021603 | 167 |
| GGGACATGGGAGGAGCCATATTGAGAAAGTAGCATGGGTACTTGGCTTCACAGAGTGTGG | LOC729170 | XM_001129548 | 168 |
| GCTGATTATTGGCATCATCTCCATTGTCCTACTCGGTTCTTAAAGGCATATGGACTTGCC | LOC654433 | AK126431 | 169 |
| AAGGTTCCATGGTAGCTAAGTGTGGACAAGCTAATCACTGAAGTTCCCTGATGCAGAGTT | NT_006713.14 | NT_006713.14 | 170 |
| ACAGCCCAGCAGGAGGAAGCATCACACAGCGTTAGGAGCCGTTTCCTTCAGGTGTTAAG | CHST10 | NM_004854 | 171 |
| AGACATTGAGTCTTTTGGGAGACAGAAGGGAGGGAGAGTGCCAGTCAAAAGGGTTTCGTG | BU953908 | BU953908 | 172 |
| ATGAGCCGATGTTGACAAGAGCTTAAGTAAGTCTCCATGTACATCAAGTACTTTGGAGAC | OFCC1 | AF520801 | 173 |
| TGAAAAGTGCACCACATGGATGTTAAGTAGAAATTCAAGAAAGTAAGATGTCTTCAGCA | C8orf4 | NM_020130 | 174 |
| GAGACAAACTCAATGTTAAAATCTCTAGGAGTGACCACGAAGTTTCATAGTTTTCCAAAT | LYPLAL1 | NM_138794 | 175 |
| GATCAGCACCTATGAGTTCGGCAAAAGCTTCTTCCAGAGGCTGAACCAGGACCGGCTTCT | SLC25A39 | NM_016016 | 176 |
| TTTAAATCTCCACAGACGTATATGGATGGTTTACTGCATTATGTATCTGTAATAAGCGAC | LAMA3 | NM_198129 | 177 |
| GGAAGGCTTCTGACGCTTGTGGCCAGACTGCAATTGCACTTATGTGTTATGCTACTAATA | ZDHHC14 | NM_153746 | 178 |
| AGAAACCAGGAACTATGTTAAACAAAGAAAAGCTTTTGGCAAAACAGTTGCTCACCTACA | ACADL | NM_001608 | 179 |

TABLE 1-continued

| 18-38/4 set4-setSequence | Gene Name | Systematic Name | SEQ ID NO |
|---|---|---|---|
| AAAGATGGTGGCTGTGTCTCTCCCCGGTAATGTCACTGTTTTTATTCCTTCCATCTAGCA | CASC3 | NM_007359 | 180 |
| CTATAAGGTTGTACTGCTGGGAAAATACAATGCACAGGGCTTAGGTTCAGATCATGAATT | PYROXD1 | NM_024854 | 181 |
| TCAATGTAAAAACTAGAACCTTTATATACTGGGGATTATAAGATTCTACTTACTAGAAAT | LCORL | AL133031 | 182 |
| GATCCCTTCTCAAACTCAGAACCCTAGCAGTGTTACCTTAAACAAAAATGAGCTCGAGAA | MGC12966 | NM_001037163 | 183 |
| AACGCTGTCCGCATCATCCAGGTCTATTGGCGCTGGAGAAGTTGCCATACCCGTGGCTTT | THC2623157 | THC2623157 | 184 |
| TGGGGACAGCCAAGTTTTGTTGATAAACCTATTTCCTAGCATGCCTTCAGGAAGTTGTGC | BTBD11 | NM_001018072 | 185 |
| TCACTCAGGACTTCTCTCCTGAAGAACACGCAGTGCTAAAACTGAGGATGATTTCCCTAA | PTPN7 | NM_080588 | 186 |
| GAACTGAACATTGTTTGTAAGGCTGTGGATGATGGTTACAATGTGCAGCCAGACACCGTG | SUOX | NM_000456 | 187 |
| GGTCTTGGTAGAAGCGCGTGCAAAAGCCATTCTGGACTTCCTGGATGCCCTGCTAGAGCT | GSDML | NM_018530 | 188 |
| GAAACAAGTGCCATGAGGCCCTCAAGCCAAACTCTTCCAACTGAATAAATGAGCTAATTC | THC2727170 | THC2727170 | 189 |
| TCACCCTGCATATCCTAGGTTTGAAGAGAAACGCTCAGATCCGCTTATTTCTGCCAGTAT | RNH1 | NM_203389 | 190 |
| TGAGCCAAGCACAGTGGTGGCAAAAGCTTATTTGTGTACAATCACTGGCTTCATACTTCC | RPP40 | NM_006638 | 191 |
| TGTGTGCATAGTTACTCAGTTTTTATGAACTGTTGTATCCTGTTAATGCATATTGCTCTG | WTAP | NM_004906 | 192 |
| TGGCACACCGTCAACAACACGATCCCTATGTCCATGTGTTCCAAGAGGTGCCAGTCAGGG | TAS1R2 | NM_152232 | 193 |
| TATGTACAGTTTACATGAATGTTCCTCAGGACATGGCATACAATGGCCTTGGAGGTCCAA | APOL6 | NM_030641 | 194 |
| AAATAGCATGTGACACAGGACAGCCATAGTATAGTGTGTCACTCGTGGTTGGTGTCCTTT | TNFRSF10B | NM_003842 | 195 |
| AGTGCTGGCCCAGAACAGGTTTCTCCTGGAGCTACAGATAAGCAACAACAGGCTGGAGGA | RNH1 | NM_002939 | 196 |
| TGTCCTTCATTCTTTTGATGTGATGTATCGCATTTACAGATCTGAATATGTATTAGGTGG | AF119879 | AF119879 | 197 |
| TGACTGTTTTAATGGGGTTTCACCCAAATTGTTTAATGCTTCTGCTGTAAATGTCATACT | INSM2 | NM_032594 | 198 |
| TGACTATGAGACCGTTCGCAATGGGGGCCTGATCTTCGCTGGACTGGCCTTCATCGTGGG | FXYD2 | NM_021603 | 199 |
| AATCCCATGGACCCTCTGGACTACAAGGATCAGAGTGCCTGGAAGTTTCAGATCTTGTAG | CRX | NM_000554 | 200 |
| ATGGGTAATATCAGCATAATTGTATTGATCAGAAGAAGTCATCATCTTCATACACCCATG | OR5P3 | NM_153445 | 201 |
| TGGAATAATGTTCTCTGCTACTTTTAACCTGATTTTCTTTGTACCTAAATAGGCAGCTAG | SIRT5 | NM_031244 | 202 |
| ACAATAAGTTCTGCAAAACCCTCTCATTCATGAAAAGGTGCTCCTTGCTAGACAGAAACT | ARID2 | NM_152641 | 203 |
| ACACGTTTTTGGAGGATACCAAGAAGCTGTACCACTCAGAAGCCTCTTCCATCAACTTCA | SERPINA1 | NM_000295 | 204 |

TABLE 1-continued

| 18-38/4 set4-setSequence | Gene Name | Systematic Name | SEQ ID NO |
|---|---|---|---|
| GGAAGGCTTCTGACGCTTGTGGCCAGACTGCAATTGCACTTATGTGTTATGCTACTAATA | ZDHHC14 | NM_153746.1 | 205 |
| GCTCTTAGAACCTCAGGTTCTCAGGCAAGAGCCACCTGCTATTGCCGAACTGGCCGTTGT | DEFA5 | NM_021010 | 206 |
| GCAGGATAAGGACAAGGCTACACAATGGCTTAGAACAGTTAATCGGGCAACAGTTGGAAA | THC2505770 | THC2505770 | 207 |
| CGCATAATTCGGCTCATCTCCTTAGCTGCCCAGAAATTCATCTCAGATATTGCCAATGAT | TAF10 | NM_006284 | 208 |
| TAACGTTTCCGGTATTACTCTGCTACACGTAGCCTTTTTACTTTTGGGGTTTTGTTTTTG | CD81 | NM_004356 | 209 |

TABLE 2

Multivariate Analysis on Validation Set

| Variable | p-value | HR | 95% CI | |
|---|---|---|---|---|
| Table 2A: All Stages (n = 208) | | | | |
| 18-gene profile | <0.001 | 3.645 | 1.808 | 7.349 |
| Positive Lymph Nodes | <0.001 | 1.286 | 1.128 | 1.467 |
| Stage 1 vs 2 Baseline = 2 | 0.198 | 0.166 | 0.022 | 1.243 |
| Stage 3 vs 2 | 0.753 | 0.323 | 1.758 | |
| Table 2B: Stage II only (n = 115) | | | | |
| 18-gene profile | 0.010 | 3.56 | 1.35-9.39 | |
| T4 | 0.065 | 2.86 | 0.94-8.74 | |
| Table 2C: Stage III only (n = 63) | | | | |
| 18-gene profile | 0.003 | 5.569 | 1.759 | 17.528 |
| Age70 | 0.012 | 5.243 | 1.455 | 18.889 |
| LN assessed | 0.197 | 0.951 | 0.882 | 1.026 |
| PosLN | 0.001 | 1.313 | 1.117 | 1.543 |
| pT | 0.007 | 0.115 | 0.024 | 0.552 |

TABLE 3

The 18-gene profile risk assessment in comparison to risk assessment by parameters described in the ASCO recommendation for stage II patients (n = 115). ASCO Recommendation defines stage II patients at high risk if the total number of assessed lymph nodes is less than 12 and/or if the tumor is T4 stage and/or if the histologic Grade is 3 and/or if the patient had an emergency presentation or obstruction.

Table 3A: Patients defined as Low or High Risk by the 18-gene profile or ASCO Recommendation: 45% of patients have a discordant assessment

| | 18-gene profile Low Risk | 18-gene profile High Risk |
|---|---|---|
| ASCO Low Risk | 43 | 27 |
| ASCO High Risk | 29 | 16 |

Table 3B: Multivariate Analysis

| Variable | p-value | HR | 95% CI |
|---|---|---|---|
| 18-gene profile | 0.009 | 3.639 | 1.373-9.644 |
| ASCO* | 0.263 | 1.696 | 0.672-4.282 |

The invention claimed is:

1. A method for typing a RNA sample of an individual suffering from colorectal cancer or suspected of suffering therefrom, the method comprising
   a. providing an RNA sample that is prepared from a tissue sample from said individual, said tissue sample comprising colorectal cancer cells or suspected to comprise colorectal cancer cells;
   b. determining RNA levels for a set of genes in said RNA sample by microarray analysis; and
   c. typing said RNA sample on the basis of the RNA levels determined for said set of genes;
   wherein said set of genes comprises at least MCTP1 comprising SEQ ID NO: 36 and THNSL2 comprising SEQ ID NO: 13.

2. The method of claim 1, wherein said set of genes further comprises LAMA3 comprising SEQ ID NO: 33, CTSC comprising SEQ ID NO: 9, PYROXD1 comprising SEQ ID NO: 5, EDEM1 comprising SEQ ID NO: 10, IL2RB comprising SEQ ID NO: 39, ZNF697 comprising SEQ ID NO: 30, SLC6A12 comprising SEQ ID NO; 12 and IL2RA comprising SEQ ID NO: 7.

3. The method of claim 1, whereby said set of genes further comprises, LAMA3 comprising SEQ ID NO: 33, CTSC comprising SEQ ID NO: 79, PYROXD1 comprising SEQ ID NO: 181, EDEM1 comprising SEQ ID NO: 10, IL2RB comprising SEQ ID NO: 39, ZNF697 comprising SEQ ID NO: 30, SLC6A12 comprising SEQ ID NO: 12, IL2RA comprising SEQ ID NO: 7, CYFIP2 comprising SEQ ID NO: 38, PIM3 comprising SEQ ID NO: 22, LIF comprising SEQ ID NO: 2, M6PRBP1 comprising SEQ ID NO: 11, CA438802 comprising SEQ ID NO: 35, HSD3B1 comprising SEQ ID NO: 37, ZBED4 comprising SEQ ID NO: 1, and PPARA comprising (SEQ ID NO: 23).

4. The method according to claim 1, further comprising normalizing the determined RNA levels of said set of genes in said sample.

5. The method according to claim 1, whereby said colorectal cancer comprises a TNM stage I, TNM stage II or TNM stage III cancer according to the TNM Staging System.

6. The method according to claim 1, whereby said typing differentiates cancer cells with a low metastasizing potential and cancer cells with a high metastatic potential.

7. A method of classifying an individual suffering from colorectal cancer, comprising:
   classifying said individual as having a poor prognosis or a good prognosis by a method comprising:
      (a) providing an RNA sample from a said individual that is prepared from a tissue sample from said individual, said tissue sample comprising colorectal cancer cells or suspected to comprise colorectal cancer cells;
      (b) determining a level of RNA for a set of genes comprising at least MCTP1 comprising SEQ ID NO: 36 and THNSL2 comprising SEQ ID NO: 13 in said sample;
      (c) determining a similarity value between a level of expression from the set of genes in said individual and a level of expression from said set of genes in a patient having no recurrent disease within five years of initial diagnosis; and
      (d) classifying said individual as having a poor prognosis if said similarity value is below a first similarity threshold value, and classifying said individual as having a good prognosis if said similarity value exceeds said first similarity threshold value.

8. The method of claim 7, whereby the determined level of RNA for said set of genes is normalized.

9. A method of assigning treatment to a individual suffering from colorectal cancer, comprising
  (a) classifying said individual as having a good prognosis or a poor prognosis according to claim 7;
  (b) assigning chemotherapy if said individual is classified as having said poor prognosis.

10. The method according to claim 1, whereby said colorectal cancer comprises a colon cancer.

11. The method according to claim 7, whereby said colorectal cancer comprises a colon cancer.

12. The method according to claim 1, whereby a ratio of expression of MCTP1 comprising SEQ ID NO: 36 and THNSL2 comprising SEQ ID NO: 13 is determined.

* * * * *

SEQUENCE LISTING

<160> NUMBER OF SEQ ID NOS: 211

<210> SEQ ID NO 1
<211> LENGTH: 60
<212> TYPE: DNA
<213> ORGANISM: Homo sapiens

<400> SEQUENCE: 1
ttagaagaga tggcttatta acagggaaga agcttgttat attccagttg taagaatagc    60

<210> SEQ ID NO 2
<211> LENGTH: 60
<212> TYPE: DNA
<213> ORGANISM: Homo sapiens

<400> SEQUENCE: 2
catttccctg cagatggtac agatgttcct gccttagagt catctctagt tccccacctc    60

<210> SEQ ID NO 3
<211> LENGTH: 60
<212> TYPE: DNA

```
<213> ORGANISM: Homo sapiens

<400> SEQUENCE: 3
gggagccttc ttgatgatct caaaaataat agctattcaa gaaaatcacc aagtgactgt    60

<210> SEQ ID NO 4
<211> LENGTH: 60
<212> TYPE: DNA
<213> ORGANISM: Homo sapiens

<400> SEQUENCE: 4
agcctgagcg tttaatttat tcagtacctg tgtttgtgtg aatgcggtgt gtgcaggcat    60

<210> SEQ ID NO 5
<211> LENGTH: 60
<212> TYPE: DNA
<213> ORGANISM: Homo sapiens

<400> SEQUENCE: 5
ttttgaagaa aaagtccttc acttttccaa gagaccatac gtcagttaca actaatacag    60

<210> SEQ ID NO 6
<211> LENGTH: 60
<212> TYPE: DNA
<213> ORGANISM: Homo sapiens

<400> SEQUENCE: 6
tccatatctt tgttttaacc agtacttcta agagcataga actcaaatgc tgggggaggt    60

<210> SEQ ID NO 7
<211> LENGTH: 60
<212> TYPE: DNA
<213> ORGANISM: Homo sapiens

<400> SEQUENCE: 7
agagaggttt ccgcagaata aaaagcgggt cactctatat gctctgtaca ggaaactcta    60

<210> SEQ ID NO 8
<211> LENGTH: 60
<212> TYPE: DNA
<213> ORGANISM: Homo sapiens

<400> SEQUENCE: 8
ttttgaagaa aaagtccttc acttttccaa gagaccatac gtcagttaca actaatacag    60

<210> SEQ ID NO 9
<211> LENGTH: 60
<212> TYPE: DNA
<213> ORGANISM: Homo sapiens

<400> SEQUENCE: 9
agtcgaaaaa tcccaaggcc caaacctgca ccactgactg ctgaaataca gcaaagatt    60

<210> SEQ ID NO 10
<211> LENGTH: 60
<212> TYPE: DNA
<213> ORGANISM: Homo sapiens

<400> SEQUENCE: 10
attaccacct gtaattcctc tttggattgt gtagactcaa catgagacat tcctttctgc    60

<210> SEQ ID NO 11
<211> LENGTH: 60
```

<212> TYPE: DNA
<213> ORGANISM: Homo sapiens

<400> SEQUENCE: 11
tctctataat gcagctgtgc tctggagtcc tcaacccggg gctcatttca aacttatttt    60

<210> SEQ ID NO 12
<211> LENGTH: 60
<212> TYPE: DNA
<213> ORGANISM: Homo sapiens

<400> SEQUENCE: 12
ggaagtgaca actgaacaca ctgtgttgga tcggaggttc cgttagggga tccttcctta    60

<210> SEQ ID NO 13
<211> LENGTH: 60
<212> TYPE: DNA
<213> ORGANISM: Homo sapiens

<400> SEQUENCE: 13
accctgatgc ggagaggtga caactggatg ctgatgcttc gggacaccat tgaggacctt    60

<210> SEQ ID NO 14
<211> LENGTH: 60
<212> TYPE: DNA
<213> ORGANISM: Homo sapiens

<400> SEQUENCE: 14
agggacctag tgaaatcaat gaaactcttg agtcttgctt aggctcgcaa acaagaagtg    60

<210> SEQ ID NO 15
<211> LENGTH: 60
<212> TYPE: DNA
<213> ORGANISM: Homo sapiens

<400> SEQUENCE: 15
aacagagggc agaaggtcta tacgtcctga ggccttttat gcaacgtttg tttgtggaat    60

<210> SEQ ID NO 16
<211> LENGTH: 60
<212> TYPE: DNA
<213> ORGANISM: Homo sapiens

<400> SEQUENCE: 16
tgaaaagcat tatcaacaga atgaggataa gatgagaaaa tccttcaatc agcagttagc    60

<210> SEQ ID NO 17
<211> LENGTH: 60
<212> TYPE: DNA
<213> ORGANISM: Homo sapiens

<400> SEQUENCE: 17
tgaaaatgaa aagtcttgat gtagtcagat ggttactctc ttaacattag gtattacccc    60

<210> SEQ ID NO 18
<211> LENGTH: 60
<212> TYPE: DNA
<213> ORGANISM: Homo sapiens

<400> SEQUENCE: 18
accctgatgc ggagaggtga caactggatg ctgatgcttc gggacaccat tgaggacctt    60

<210> SEQ ID NO 19

```
<211> LENGTH: 60
<212> TYPE: DNA
<213> ORGANISM: Homo sapiens

<400> SEQUENCE: 19
agaggccttg aatactcaga aaatgggaga ttgtgaatgg gtgtagagga tatctatgaa      60

<210> SEQ ID NO 20
<211> LENGTH: 60
<212> TYPE: DNA
<213> ORGANISM: Homo sapiens

<400> SEQUENCE: 20
aaggaaaatg aatactgtgt aatagttaaa cccattcata ggttgcaata gagtgtcagc      60

<210> SEQ ID NO 21
<211> LENGTH: 60
<212> TYPE: DNA
<213> ORGANISM: Homo sapiens

<400> SEQUENCE: 21
gaagcttttg tcagtaacct caatggaacc accgtgctgg aaatcaccca gggattgtgc      60

<210> SEQ ID NO 22
<211> LENGTH: 60
<212> TYPE: DNA
<213> ORGANISM: Homo sapiens

<400> SEQUENCE: 22
agcctgagcg tttaatttat tcagtacctg tgtttgtgtg aatgcggtgt gtgcaggcat      60

<210> SEQ ID NO 23
<211> LENGTH: 60
<212> TYPE: DNA
<213> ORGANISM: Homo sapiens

<400> SEQUENCE: 23
acggttattg accccataga ctagggtaag aataaaggca ataaatttgg tctgactcag      60

<210> SEQ ID NO 24
<211> LENGTH: 60
<212> TYPE: DNA
<213> ORGANISM: Homo sapiens

<400> SEQUENCE: 24
ccaaaacgcc attgccttcc gcagagacca gagatctctg tacttcaagg acagccttgg      60

<210> SEQ ID NO 25
<211> LENGTH: 60
<212> TYPE: DNA
<213> ORGANISM: Homo sapiens

<400> SEQUENCE: 25
aagaactacc gggagacaag aaagggacac tctctagaga aggcttcaag gaaagcttat      60

<210> SEQ ID NO 26
<211> LENGTH: 60
<212> TYPE: DNA
<213> ORGANISM: Homo sapiens

<400> SEQUENCE: 26
tctcattcca gcatgagcgt ttctgagtct cttcaagacg aatctagttt tcaccttcac      60
```

```
<210> SEQ ID NO 27
<211> LENGTH: 60
<212> TYPE: DNA
<213> ORGANISM: Homo sapiens

<400> SEQUENCE: 27
agatctttgt aggtttagac atggctccct gtctccagta aacatccagc cattcagaca      60

<210> SEQ ID NO 28
<211> LENGTH: 60
<212> TYPE: DNA
<213> ORGANISM: Homo sapiens

<400> SEQUENCE: 28
agttccagat gtacatggta tattttgaag tagaaataaa agaattactt attttttctaa    60

<210> SEQ ID NO 29
<211> LENGTH: 60
<212> TYPE: DNA
<213> ORGANISM: Homo sapiens

<400> SEQUENCE: 29
ctccatctta ttttcatgta tatgtgttca ttaaagcatg aatggtatgg aactctctcc    60

<210> SEQ ID NO 30
<211> LENGTH: 60
<212> TYPE: DNA
<213> ORGANISM: Homo sapiens

<400> SEQUENCE: 30
aacctggagc aatttaaata ggctaaatgg ttttgattaa atcttgagct ccgagttgga    60

<210> SEQ ID NO 31
<211> LENGTH: 60
<212> TYPE: DNA
<213> ORGANISM: Homo sapiens

<400> SEQUENCE: 31
actgatgact gcgcctgtgt tccagaactg ttccgtctcc ctgagatcta ttccctccac    60

<210> SEQ ID NO 32
<211> LENGTH: 60
<212> TYPE: DNA
<213> ORGANISM: Homo sapiens

<400> SEQUENCE: 32
gaaatgttca gcagattttg gttttgaatt ttctttcatc agtatcaccc atatgagcag    60

<210> SEQ ID NO 33
<211> LENGTH: 60
<212> TYPE: DNA
<213> ORGANISM: Homo sapiens

<400> SEQUENCE: 33
tctaattttg aattctgacc atggatacccc atcactttgg cattcagtgc tacatgtgta   60

<210> SEQ ID NO 34
<211> LENGTH: 60
<212> TYPE: DNA
<213> ORGANISM: Homo sapiens

<400> SEQUENCE: 34
caatacccat ctcgtgtatt aatcccatca atcattcagg tgtctggaat acaattcttt    60
```

```
<210> SEQ ID NO 35
<211> LENGTH: 60
<212> TYPE: DNA
<213> ORGANISM: Homo sapiens

<400> SEQUENCE: 35
tgatctttca cttgttaact agggaaaaac actagtcacc agtgtggtac aaacttgtac      60

<210> SEQ ID NO 36
<211> LENGTH: 60
<212> TYPE: DNA
<213> ORGANISM: Homo sapiens

<400> SEQUENCE: 36
tgtgtggtag aactgaacaa cgatagactg ctaacacata ctgtctacaa aaatctcaat      60

<210> SEQ ID NO 37
<211> LENGTH: 60
<212> TYPE: DNA
<213> ORGANISM: Homo sapiens

<400> SEQUENCE: 37
aagtccaaga ctcagtgatc gaaggatgac agagatgtgc agtgggtatt gttaggagat      60

<210> SEQ ID NO 38
<211> LENGTH: 60
<212> TYPE: DNA
<213> ORGANISM: Homo sapiens

<400> SEQUENCE: 38
acattacctt caggagactt gatcccagta gactgaggtc ttccctttca gcagaaagat      60

<210> SEQ ID NO 39
<211> LENGTH: 60
<212> TYPE: DNA
<213> ORGANISM: Homo sapiens

<400> SEQUENCE: 39
ttgaggttgt ctgagtcttg ggtctatgcc ttgaaaaaag ctgaattatt ggacagtctc      60

<210> SEQ ID NO 40
<211> LENGTH: 60
<212> TYPE: DNA
<213> ORGANISM: Homo sapiens

<400> SEQUENCE: 40
cattgtcagt gctacaggag ttacaccaaa tgtagaacct tttctccatg gtaacagttt      60

<210> SEQ ID NO 41
<211> LENGTH: 60
<212> TYPE: DNA
<213> ORGANISM: Homo sapiens

<400> SEQUENCE: 41
cagaggtggg gccatagaat cctacactac agctttcagt tttttagaaa atgtgataat      60

<210> SEQ ID NO 42
<211> LENGTH: 60
<212> TYPE: DNA
<213> ORGANISM: Homo sapiens

<400> SEQUENCE: 42
cagcctttcc tcatgtcaac acagttcaca atatagtttt caaagtacag tttaaaactc      60
```

<210> SEQ ID NO 43
<211> LENGTH: 60
<212> TYPE: DNA
<213> ORGANISM: Homo sapiens

<400> SEQUENCE: 43
tgggagagcg ttggtggatg tgttctgcat gttcctttct gtacagtaac ttctgcattt    60

<210> SEQ ID NO 44
<211> LENGTH: 60
<212> TYPE: DNA
<213> ORGANISM: Homo sapiens

<400> SEQUENCE: 44
ttgctttgaa aagcttcctc caaaagctgt attgtggtac ttttgactct gggacaagag    60

<210> SEQ ID NO 45
<211> LENGTH: 60
<212> TYPE: DNA
<213> ORGANISM: Homo sapiens

<400> SEQUENCE: 45
cacagatgtt tttcaagttc ctcagtttgt actgaaatta gggattcatc agggcaggaa    60

<210> SEQ ID NO 46
<211> LENGTH: 60
<212> TYPE: DNA
<213> ORGANISM: Homo sapiens

<400> SEQUENCE: 46
gtaatgcctg gccgcagtgt gtgtgtatcc catacccac tctggaagga accatccagt     60

<210> SEQ ID NO 47
<211> LENGTH: 60
<212> TYPE: DNA
<213> ORGANISM: Homo sapiens

<400> SEQUENCE: 47
cattgtcagt gctacaggag ttacaccaaa tgtagaacct tttctccatg gtaacagttt    60

<210> SEQ ID NO 48
<211> LENGTH: 60
<212> TYPE: DNA
<213> ORGANISM: Homo sapiens

<400> SEQUENCE: 48
aacagttaac aggatgcaga catggcagag gtttcctaaa aatctcatta tctataacca    60

<210> SEQ ID NO 49
<211> LENGTH: 60
<212> TYPE: DNA
<213> ORGANISM: Homo sapiens

<400> SEQUENCE: 49
ccagggttgt agccctggat actatcggga tcataaaggc ttgtataccg gacggtgtgt    60

<210> SEQ ID NO 50
<211> LENGTH: 60
<212> TYPE: DNA
<213> ORGANISM: Homo sapiens

<400> SEQUENCE: 50
atacatttta attcctcacg ttttatattg gagagttcgg tacagactgt ccattactgc    60

<210> SEQ ID NO 51
<211> LENGTH: 60
<212> TYPE: DNA
<213> ORGANISM: Homo sapiens

<400> SEQUENCE: 51
tttaaatctc cacagacgta tatggatggt ttactgcatt atgtatctgt aataagcgac    60

<210> SEQ ID NO 52
<211> LENGTH: 60
<212> TYPE: DNA
<213> ORGANISM: Homo sapiens

<400> SEQUENCE: 52
ttcgtcacct gtagagcgtt tgtcactgtt catctggtat taaagattcc acattctcat    60

<210> SEQ ID NO 53
<211> LENGTH: 60
<212> TYPE: DNA
<213> ORGANISM: Homo sapiens

<400> SEQUENCE: 53
ccccacaggc catgaccttg aagtgaaagt cttctgttgc tattgtgggc tcaaatattt    60

<210> SEQ ID NO 54
<211> LENGTH: 60
<212> TYPE: DNA
<213> ORGANISM: Homo sapiens

<400> SEQUENCE: 54
gtgagttcat ggaagtctaa atcagtaatt tagaggatag tgacactcaa tcagtttgta    60

<210> SEQ ID NO 55
<211> LENGTH: 60
<212> TYPE: DNA
<213> ORGANISM: Homo sapiens

<400> SEQUENCE: 55
tgcagagaga atgtcttcat agagagaatg tcattaaata cttgaatctg catgacagtt    60

<210> SEQ ID NO 56
<211> LENGTH: 60
<212> TYPE: DNA
<213> ORGANISM: Homo sapiens

<400> SEQUENCE: 56
tagatgaatg gattatctgc actgattggg atgtcggttt tagagagggt caacagtatg    60

<210> SEQ ID NO 57
<211> LENGTH: 60
<212> TYPE: DNA
<213> ORGANISM: Homo sapiens

<400> SEQUENCE: 57
atcttagaaa caccttgaag tatgccaaga aaaacgtccg tgcattttgg aaactcagag    60

<210> SEQ ID NO 58
<211> LENGTH: 60
<212> TYPE: DNA
<213> ORGANISM: Homo sapiens

<400> SEQUENCE: 58
agattacatt aattttcta taaattggaa gatttataaa tgtttgaaat tgtacacatt    60

<210> SEQ ID NO 59
<211> LENGTH: 60
<212> TYPE: DNA
<213> ORGANISM: Homo sapiens

<400> SEQUENCE: 59
cagtggaact gatggacaca agcttatcgc cacactggtt ttcctctgaa acaaggccct    60

<210> SEQ ID NO 60
<211> LENGTH: 60
<212> TYPE: DNA
<213> ORGANISM: Homo sapiens

<400> SEQUENCE: 60
cctggataac ctgaggcgag tcatgccatg ctactctaaa acccaaaaac tttccaagat    60

<210> SEQ ID NO 61
<211> LENGTH: 60
<212> TYPE: DNA
<213> ORGANISM: Homo sapiens

<400> SEQUENCE: 61
atgtaactga ttttctgcta gaagtttgat atcctctgaa tttagctaaa ggatcaccag    60

<210> SEQ ID NO 62
<211> LENGTH: 60
<212> TYPE: DNA
<213> ORGANISM: Homo sapiens

<400> SEQUENCE: 62
caagttttcc ttgctttcct gatactcttt ggcgctgact tggaattcta agagccttgg    60

<210> SEQ ID NO 63
<211> LENGTH: 60
<212> TYPE: DNA
<213> ORGANISM: Homo sapiens

<400> SEQUENCE: 63
catattccat ttttaagaag aggtgttcca gttctgcatc tgataccgtc tcctttccct    60

<210> SEQ ID NO 64
<211> LENGTH: 60
<212> TYPE: DNA
<213> ORGANISM: Homo sapiens

<400> SEQUENCE: 64
tgatcgagaa gctgctcaat tatgcacccc tggagaagtg accacgctga aacccaccca    60

<210> SEQ ID NO 65
<211> LENGTH: 60
<212> TYPE: DNA
<213> ORGANISM: Homo sapiens

<400> SEQUENCE: 65
ttgaggttgt ctgagtcttg ggtctatgcc ttgaaaaaag ctgaattatt ggacagtctc    60

<210> SEQ ID NO 66
<211> LENGTH: 60
<212> TYPE: DNA
<213> ORGANISM: Homo sapiens

<400> SEQUENCE: 66
ttcttgccct aaacaagcaa agaaaatgca gaggtctcat ccttaagact cagaagctaa    60

<210> SEQ ID NO 67
<211> LENGTH: 60
<212> TYPE: DNA
<213> ORGANISM: Homo sapiens

<400> SEQUENCE: 67
cagactctcc acatgtgctc tactagtgag tgccttatac tctcagtatt ttggggctta    60

<210> SEQ ID NO 68
<211> LENGTH: 60
<212> TYPE: DNA
<213> ORGANISM: Homo sapiens

<400> SEQUENCE: 68
cagcctttcc tcatgtcaac acagttcaca atatagtttt caaagtacag tttaaaactc    60

<210> SEQ ID NO 69
<211> LENGTH: 60
<212> TYPE: DNA
<213> ORGANISM: Homo sapiens

<400> SEQUENCE: 69
gcaatgagtg aactgactgt ggctacattc ttgaagatat acgggagaga cgtattatta    60

<210> SEQ ID NO 70
<211> LENGTH: 60
<212> TYPE: DNA
<213> ORGANISM: Homo sapiens

<400> SEQUENCE: 70
aacagttaac aggatgcaga catggcagag gtttcctaaa aatctcatta tctataacca    60

<210> SEQ ID NO 71
<211> LENGTH: 60
<212> TYPE: DNA
<213> ORGANISM: Homo sapiens

<400> SEQUENCE: 71
ccaaatttat gtggttgtta cacttccata gttgtcttag ccgaatcctt ccatattctt    60

<210> SEQ ID NO 72
<211> LENGTH: 60
<212> TYPE: DNA
<213> ORGANISM: Homo sapiens

<400> SEQUENCE: 72
ttccagatga gctcttcttt cctacaagtt ttcataatta gggaatgcca gggtttaggg    60

<210> SEQ ID NO 73
<211> LENGTH: 60
<212> TYPE: DNA
<213> ORGANISM: Homo sapiens

<400> SEQUENCE: 73
gtaatatgtg aagattaatg gcaatgaagc aaacgtgcat aagaaaatcc acgcagcaaa    60

<210> SEQ ID NO 74
<211> LENGTH: 60
<212> TYPE: DNA
<213> ORGANISM: Homo sapiens

```
<400> SEQUENCE: 74
gcaaacttgg cagtcataaa cccacatcta ctctaacaag tctgaatggt gcataagtac    60

<210> SEQ ID NO 75
<211> LENGTH: 60
<212> TYPE: DNA
<213> ORGANISM: Homo sapiens

<400> SEQUENCE: 75
ttggttgtga gatccagaat aacagaagca ctggagcatt ctggaagaat gcctatgatg    60

<210> SEQ ID NO 76
<211> LENGTH: 60
<212> TYPE: DNA
<213> ORGANISM: Homo sapiens

<400> SEQUENCE: 76
cttctgttag ctctggactc ttaacactta agttactctt ctgaaattgc taggaccatt    60

<210> SEQ ID NO 77
<211> LENGTH: 60
<212> TYPE: DNA
<213> ORGANISM: Homo sapiens

<400> SEQUENCE: 77
tgtacctact gatggtgctg taaccacctc acagattcca gcttcggaac aagagaccct    60

<210> SEQ ID NO 78
<211> LENGTH: 60
<212> TYPE: DNA
<213> ORGANISM: Homo sapiens

<400> SEQUENCE: 78
tttgatgtag ctctaccgat actatgtggt aatgctattt tgttttacta acaagctctg    60

<210> SEQ ID NO 79
<211> LENGTH: 60
<212> TYPE: DNA
<213> ORGANISM: Homo sapiens

<400> SEQUENCE: 79
cactcccttg gaaaacagta aacatcattt tggaatgtga acaaccagag actacacagg    60

<210> SEQ ID NO 80
<211> LENGTH: 60
<212> TYPE: DNA
<213> ORGANISM: Homo sapiens

<400> SEQUENCE: 80
atcttagaaa caccttgaag tatgccaaga aaaacgtccg tgcattttgg aaactcagag    60

<210> SEQ ID NO 81
<211> LENGTH: 60
<212> TYPE: DNA
<213> ORGANISM: Homo sapiens

<400> SEQUENCE: 81
tcctgacaag ttttctccc atgtccgaga tggccttaat tttggtacac agattggctt    60

<210> SEQ ID NO 82
<211> LENGTH: 60
<212> TYPE: DNA
```

<213> ORGANISM: Homo sapiens

<400> SEQUENCE: 82
agtgactcat ttaccaacat taaaccctag gatagatgca acagagaagt actacttcct      60

<210> SEQ ID NO 83
<211> LENGTH: 60
<212> TYPE: DNA
<213> ORGANISM: Homo sapiens

<400> SEQUENCE: 83
tgagcagctt gtgaatgtaa ctgatgatct actcatatat aagatcagat tggaaaaagc      60

<210> SEQ ID NO 84
<211> LENGTH: 60
<212> TYPE: DNA
<213> ORGANISM: Homo sapiens

<400> SEQUENCE: 84
gttcgagagc cgagtctgtg ggcactctct gccttcatgc acctgtcctt tctaacacgt      60

<210> SEQ ID NO 85
<211> LENGTH: 60
<212> TYPE: DNA
<213> ORGANISM: Homo sapiens

<400> SEQUENCE: 85
aagctgtgcc tcgacacatc ctcatcccaa gcatgggaca cctcaagatg aataataatt      60

<210> SEQ ID NO 86
<211> LENGTH: 60
<212> TYPE: DNA
<213> ORGANISM: Homo sapiens

<400> SEQUENCE: 86
aatatttgtg taacggagat atactactgt aagttttgta ctgtactggc tgaaagtctg      60

<210> SEQ ID NO 87
<211> LENGTH: 60
<212> TYPE: DNA
<213> ORGANISM: Homo sapiens

<400> SEQUENCE: 87
gcctttagtt ctccactggg gaggaatcct ggaccaagca caaaaactta acaaaagtga      60

<210> SEQ ID NO 88
<211> LENGTH: 60
<212> TYPE: DNA
<213> ORGANISM: Homo sapiens

<400> SEQUENCE: 88
tttgtgaaat aatgtaccat agactctcac caactgtata tacctgtaca tatcagaagc      60

<210> SEQ ID NO 89
<211> LENGTH: 60
<212> TYPE: DNA
<213> ORGANISM: Homo sapiens

<400> SEQUENCE: 89
aaggttccat ggtagctaag tgtggacaag ctaatcactg aagttccctg atgcagagtt      60

<210> SEQ ID NO 90
<211> LENGTH: 60

<212> TYPE: DNA
<213> ORGANISM: Homo sapiens

<400> SEQUENCE: 90
tatgtacagt ttacatgaat gttcctcagg acatggcata caatggcctt ggaggtccaa        60

<210> SEQ ID NO 91
<211> LENGTH: 60
<212> TYPE: DNA
<213> ORGANISM: Homo sapiens

<400> SEQUENCE: 91
tattgtaaac tttgtggctt ttggtctgtg atgcttggtc tcaaaggaaa aaataagatg        60

<210> SEQ ID NO 92
<211> LENGTH: 60
<212> TYPE: DNA
<213> ORGANISM: Homo sapiens

<400> SEQUENCE: 92
acattaacca gctcctgaga accatgtcta tgcccaaagg tagagttctg gataaaaacc        60

<210> SEQ ID NO 93
<211> LENGTH: 60
<212> TYPE: DNA
<213> ORGANISM: Homo sapiens

<400> SEQUENCE: 93
tgaacatgga ggatgaccag aactggtaca aggccgagct ccggggtgtc gagggattta        60

<210> SEQ ID NO 94
<211> LENGTH: 60
<212> TYPE: DNA
<213> ORGANISM: Homo sapiens

<400> SEQUENCE: 94
caacaccatc ctcatctgca tggtgatcct gctgaacatc ggcctggcca tcctctttgt        60

<210> SEQ ID NO 95
<211> LENGTH: 60
<212> TYPE: DNA
<213> ORGANISM: Homo sapiens

<400> SEQUENCE: 95
gtgtggaaac atctatccta tagatcatcc tattcttatg tgtctttggt tatcagatca        60

<210> SEQ ID NO 96
<211> LENGTH: 60
<212> TYPE: DNA
<213> ORGANISM: Homo sapiens

<400> SEQUENCE: 96
agtttcctat gtttcactgt gcaaatatat ctgctattct ccatactctg taacagttgc        60

<210> SEQ ID NO 97
<211> LENGTH: 60
<212> TYPE: DNA
<213> ORGANISM: Homo sapiens

<400> SEQUENCE: 97
gaaggacaat gtctgaatta aatgccgtgc tttaaactga aagggaaact tagcaaataa        60

<210> SEQ ID NO 98

<211> LENGTH: 60
<212> TYPE: DNA
<213> ORGANISM: Homo sapiens

<400> SEQUENCE: 98
atacaaagtg caaaaaagct tggctccttc tgtattcttt aaaaacaaaa caacaacaaa    60

<210> SEQ ID NO 99
<211> LENGTH: 60
<212> TYPE: DNA
<213> ORGANISM: Homo sapiens

<400> SEQUENCE: 99
caagcttcct tctttctaac ccccagactt tggcctctga gtgaaatgtc tctctttgcc    60

<210> SEQ ID NO 100
<211> LENGTH: 60
<212> TYPE: DNA
<213> ORGANISM: Homo sapiens

<400> SEQUENCE: 100
agacaatggg aaagtaagtt ataaaaaata ctgggaaatc tgtttctctt ctgagcaagc    60

<210> SEQ ID NO 101
<211> LENGTH: 60
<212> TYPE: DNA
<213> ORGANISM: Homo sapiens

<400> SEQUENCE: 101
cgcagccttc ggtatcccct gcacagataa gtttgtcgtc ttttcacaga ttgagatatt    60

<210> SEQ ID NO 102
<211> LENGTH: 60
<212> TYPE: DNA
<213> ORGANISM: Homo sapiens

<400> SEQUENCE: 102
aaatgccatg cggttttttca acttctcatg gagggtcact gccgatcagc tcaggaaagc    60

<210> SEQ ID NO 103
<211> LENGTH: 60
<212> TYPE: DNA
<213> ORGANISM: Homo sapiens

<400> SEQUENCE: 103
aacaacgggt ttctgttcca actggttgat caacttcttg agtcaacaag tcccaaaacc    60

<210> SEQ ID NO 104
<211> LENGTH: 60
<212> TYPE: DNA
<213> ORGANISM: Homo sapiens

<400> SEQUENCE: 104
gatggatcca ctggaggtta agacatgtgg taagacagtg taataggaag ctgctcagtt    60

<210> SEQ ID NO 105
<211> LENGTH: 60
<212> TYPE: DNA
<213> ORGANISM: Homo sapiens

<400> SEQUENCE: 105
gtggggaggg ttcttgggt ttcttgaagc cagtatttcc catagtatct tacgtcccag    60

<210> SEQ ID NO 106
<211> LENGTH: 60
<212> TYPE: DNA
<213> ORGANISM: Homo sapiens

<400> SEQUENCE: 106
taaacagtaa ataagtact catccgataa attcaaagta attttagaac attttgacca    60

<210> SEQ ID NO 107
<211> LENGTH: 60
<212> TYPE: DNA
<213> ORGANISM: Homo sapiens

<400> SEQUENCE: 107
acagctctag aaatccttat gccatttgca actacatacc tttgtgagtt gggattttca    60

<210> SEQ ID NO 108
<211> LENGTH: 60
<212> TYPE: DNA
<213> ORGANISM: Homo sapiens

<400> SEQUENCE: 108
acactaaaag ttgcttctaa taggtggcat atgtctctgc tgtgaatgac atgaccttac    60

<210> SEQ ID NO 109
<211> LENGTH: 60
<212> TYPE: DNA
<213> ORGANISM: Homo sapiens

<400> SEQUENCE: 109
ctgatggatg agaagtttac atgcaatgat ttctagtagc aggttcgtat aattttcac    60

<210> SEQ ID NO 110
<211> LENGTH: 60
<212> TYPE: DNA
<213> ORGANISM: Homo sapiens

<400> SEQUENCE: 110
cggcctccgc ggtggacgtg ttcttttcta agccatggag tgagtgagca ggtgtgaaat    60

<210> SEQ ID NO 111
<211> LENGTH: 60
<212> TYPE: DNA
<213> ORGANISM: Homo sapiens

<400> SEQUENCE: 111
agttacagaa gcctgggtaa ctgcagcttc ttcacagaga ctggttagca accagaggca    60

<210> SEQ ID NO 112
<211> LENGTH: 60
<212> TYPE: DNA
<213> ORGANISM: Homo sapiens

<400> SEQUENCE: 112
gccaaaggtt aagacaattg aacttgaagg aggtcttttg gaagatcact ttgaaactac    60

<210> SEQ ID NO 113
<211> LENGTH: 60
<212> TYPE: DNA
<213> ORGANISM: Homo sapiens

<400> SEQUENCE: 113
ggtattttga agtactgggc ttatatttaa ttggaataca tgtgtacagc aataagcagg    60

<210> SEQ ID NO 114
<211> LENGTH: 60
<212> TYPE: DNA
<213> ORGANISM: Homo sapiens

<400> SEQUENCE: 114
ctgagcccaa aactcaaagc caaacctgtc agctctctga atgagtgcac gaccaaggat    60

<210> SEQ ID NO 115
<211> LENGTH: 60
<212> TYPE: DNA
<213> ORGANISM: Homo sapiens

<400> SEQUENCE: 115
aaagcttggt gttttctctg ggtacacccc aagcagcgtc tcctttggga tacagttatt    60

<210> SEQ ID NO 116
<211> LENGTH: 60
<212> TYPE: DNA
<213> ORGANISM: Homo sapiens

<400> SEQUENCE: 116
atctttatct atgatgcttt caagaagatg atcaagcttg cagattacta ccccatcaac    60

<210> SEQ ID NO 117
<211> LENGTH: 60
<212> TYPE: DNA
<213> ORGANISM: Homo sapiens

<400> SEQUENCE: 117
agtcacagtt accgcgtgta ctacaatgcc ggccccaagg atgaggacca ggactacatc    60

<210> SEQ ID NO 118
<211> LENGTH: 60
<212> TYPE: DNA
<213> ORGANISM: Homo sapiens

<400> SEQUENCE: 118
tgtgagatgt tcccctgct gtaaatgcag gtctcttggt atttattgag ctttgtggga    60

<210> SEQ ID NO 119
<211> LENGTH: 60
<212> TYPE: DNA
<213> ORGANISM: Homo sapiens

<400> SEQUENCE: 119
aaactcaaag agaaggaggg agatccggtg tccttattac atacaagact caggaaccca    60

<210> SEQ ID NO 120
<211> LENGTH: 60
<212> TYPE: DNA
<213> ORGANISM: Homo sapiens

<400> SEQUENCE: 120
cctagctgga ctcatggttc ctaaataacc acgctcagaa gctctgctag gacttacccc    60

<210> SEQ ID NO 121
<211> LENGTH: 60
<212> TYPE: DNA
<213> ORGANISM: Homo sapiens

<400> SEQUENCE: 121
tattgttaag tttctgttga cgggttagag agcacgggtt tggctgtgtg ctggttattc    60

<210> SEQ ID NO 122
<211> LENGTH: 60
<212> TYPE: DNA
<213> ORGANISM: Homo sapiens

<400> SEQUENCE: 122
caaaagcaag tcatggctag agtatccatg caaggtgtct tgttgcatgg aagggatagt    60

<210> SEQ ID NO 123
<211> LENGTH: 60
<212> TYPE: DNA
<213> ORGANISM: Homo sapiens

<400> SEQUENCE: 123
gagatgcctg tgtaatttcg tccgaagctg ccaggaagaa gaacagaact ttgtgtgttt    60

<210> SEQ ID NO 124
<211> LENGTH: 60
<212> TYPE: DNA
<213> ORGANISM: Homo sapiens

<400> SEQUENCE: 124
aaagaggaat cgggaaaccc tgggtaaaag tcgtccaagt ggaacttcct ttggtcgggg    60

<210> SEQ ID NO 125
<211> LENGTH: 60
<212> TYPE: DNA
<213> ORGANISM: Homo sapiens

<400> SEQUENCE: 125
aaaggaaacg cgacgaagaa cttgccaaat ctatggccat atccttgtct aaaatgtata    60

<210> SEQ ID NO 126
<211> LENGTH: 60
<212> TYPE: DNA
<213> ORGANISM: Homo sapiens

<400> SEQUENCE: 126
caaagatgca tttacctctg tatcaactca ggaaatctca taagctggta ccactcagga    60

<210> SEQ ID NO 127
<211> LENGTH: 60
<212> TYPE: DNA
<213> ORGANISM: Homo sapiens

<400> SEQUENCE: 127
ctgccccgga tgtggccgag gggcttcacc ctgtgtcctt aggaggggggt ggccttgagg    60

<210> SEQ ID NO 128
<211> LENGTH: 60
<212> TYPE: DNA
<213> ORGANISM: Homo sapiens

<400> SEQUENCE: 128
ggctgaacta caagtgtagg ccaccattat aatttataaa tacagcatac ttcaaaactg    60

<210> SEQ ID NO 129
<211> LENGTH: 60
<212> TYPE: DNA
<213> ORGANISM: Homo sapiens

<400> SEQUENCE: 129

```
ccgtctctct gcacagcaca gaaattctca atcactgaaa tgagtaactg caaataaat      60
```

<210> SEQ ID NO 130
<211> LENGTH: 60
<212> TYPE: DNA
<213> ORGANISM: Homo sapiens

<400> SEQUENCE: 130

```
ggtcttggta gaagcgcgtg caaaagccat tctggacttc ctggatgccc tgctagagct      60
```

<210> SEQ ID NO 131
<211> LENGTH: 60
<212> TYPE: DNA
<213> ORGANISM: Homo sapiens

<400> SEQUENCE: 131

```
agaactggaa gcttggagga aagcatactg gagaataagc tacaaagagc ctgggcttaa      60
```

<210> SEQ ID NO 132
<211> LENGTH: 60
<212> TYPE: DNA
<213> ORGANISM: Homo sapiens

<400> SEQUENCE: 132

```
agaagtggaa ccgcttacta cagaagggat gggttgactt ttttgttcca aagttttcca      60
```

<210> SEQ ID NO 133
<211> LENGTH: 60
<212> TYPE: DNA
<213> ORGANISM: Homo sapiens

<400> SEQUENCE: 133

```
gactgtggaa tggaatgact ctccagagct gcagattgaa ggcatatttt catctgactt      60
```

<210> SEQ ID NO 134
<211> LENGTH: 60
<212> TYPE: DNA
<213> ORGANISM: Homo sapiens

<400> SEQUENCE: 134

```
tgcttttgtc atagttccac tctctcagat acatgtatct aatgaaactg ataaatccg      60
```

<210> SEQ ID NO 135
<211> LENGTH: 60
<212> TYPE: DNA
<213> ORGANISM: Homo sapiens

<400> SEQUENCE: 135

```
gacccagtca caccatccat gaaaagctgt ttctataata tgaaaaattg ttaaatgacg      60
```

<210> SEQ ID NO 136
<211> LENGTH: 60
<212> TYPE: DNA
<213> ORGANISM: Homo sapiens

<400> SEQUENCE: 136

```
attaccctat ttcactgttg ttcaagtaaa tctaaaccct gtagacaagt gagtcatctg      60
```

<210> SEQ ID NO 137
<211> LENGTH: 60
<212> TYPE: DNA
<213> ORGANISM: Homo sapiens

<400> SEQUENCE: 137
tcacgcccac accagatgat gctgtgtttc gctggctcag cactgtctat gctggcagta    60

<210> SEQ ID NO 138
<211> LENGTH: 60
<212> TYPE: DNA
<213> ORGANISM: Homo sapiens

<400> SEQUENCE: 138
accatgtgga gatgtttctg gacttgctag agcctgctta gctgcatgtt ttgtagttac    60

<210> SEQ ID NO 139
<211> LENGTH: 60
<212> TYPE: DNA
<213> ORGANISM: Homo sapiens

<400> SEQUENCE: 139
tgaagacagt ccctatccta gaggggttga gctttcttcc tccttgggtt ggaggagacc    60

<210> SEQ ID NO 140
<211> LENGTH: 60
<212> TYPE: DNA
<213> ORGANISM: Homo sapiens

<400> SEQUENCE: 140
ttggagaatg tgtaattaga gaactataag ataaagagat aatctttaga atttgaatgt    60

<210> SEQ ID NO 141
<211> LENGTH: 60
<212> TYPE: DNA
<213> ORGANISM: Homo sapiens

<400> SEQUENCE: 141
gaagacactc cagaaaatac agaaactgca tctgtgtgca ccaaggtctg aaaaatgact    60

<210> SEQ ID NO 142
<211> LENGTH: 60
<212> TYPE: DNA
<213> ORGANISM: Homo sapiens

<400> SEQUENCE: 142
ggtcttggta gaagcgcgtg caaaagccat tctggacttc ctggatgccc tgctagagct    60

<210> SEQ ID NO 143
<211> LENGTH: 60
<212> TYPE: DNA
<213> ORGANISM: Homo sapiens

<400> SEQUENCE: 143
cagcctttcc tcatgtcaac acagttcaca atatagtttt caaagtacag tttaaaactc    60

<210> SEQ ID NO 144
<211> LENGTH: 60
<212> TYPE: DNA
<213> ORGANISM: Homo sapiens

<400> SEQUENCE: 144
tttgtgtatc aagtcccact atcaaggata agccagtcca gattcggcct tggaatctca    60

<210> SEQ ID NO 145
<211> LENGTH: 60
<212> TYPE: DNA
<213> ORGANISM: Homo sapiens

<400> SEQUENCE: 145
gaagacactc cagaaaatac agaaactgca tctgtgtgca ccaaggtctg aaaaatgact     60

<210> SEQ ID NO 146
<211> LENGTH: 60
<212> TYPE: DNA
<213> ORGANISM: Homo sapiens

<400> SEQUENCE: 146
aagaacgaaa gaatagttag gataccaatg agtaaaaggg ttcctgttca ctctgactct     60

<210> SEQ ID NO 147
<211> LENGTH: 60
<212> TYPE: DNA
<213> ORGANISM: Homo sapiens

<400> SEQUENCE: 147
ggccatacgc catgccatag cttgtgctat ctgtaaatat gagacttgta aagaactgcc     60

<210> SEQ ID NO 148
<211> LENGTH: 60
<212> TYPE: DNA
<213> ORGANISM: Homo sapiens

<400> SEQUENCE: 148
ctgccctgtg ttcgtggtgc agtggctgtt tgacgaggca cagctgacgg tggacaacgt     60

<210> SEQ ID NO 149
<211> LENGTH: 60
<212> TYPE: DNA
<213> ORGANISM: Homo sapiens

<400> SEQUENCE: 149
gctcagggaa ggggctggga tcggaacttc ctgctcttgt ttctggacaa ctttcccctt     60

<210> SEQ ID NO 150
<211> LENGTH: 60
<212> TYPE: DNA
<213> ORGANISM: Homo sapiens

<400> SEQUENCE: 150
ctttagacct tgtccccgt cactgccagc gcttgggctg aaggaagctc cagactcaat     60

<210> SEQ ID NO 151
<211> LENGTH: 60
<212> TYPE: DNA
<213> ORGANISM: Homo sapiens

<400> SEQUENCE: 151
cccagtggaa aatcgcttat atacctatga ccacacaacc atcctggccg tggtggctgt     60

<210> SEQ ID NO 152
<211> LENGTH: 60
<212> TYPE: DNA
<213> ORGANISM: Homo sapiens

<400> SEQUENCE: 152
ttttgatgag aatgaatctt ggtacttaga tgacaacatc aaaacatact ctgatcaccc     60

<210> SEQ ID NO 153
<211> LENGTH: 60
<212> TYPE: DNA
<213> ORGANISM: Homo sapiens

<400> SEQUENCE: 153
gcaaagcctt caaaatgtat cgtgcttgaa ttttgactct tctgaaatag aataactgac    60

<210> SEQ ID NO 154
<211> LENGTH: 60
<212> TYPE: DNA
<213> ORGANISM: Homo sapiens

<400> SEQUENCE: 154
aggatttcaa ggaagtgttt gctattcagg aaacaaatgg gaacagttga ctggtttagt    60

<210> SEQ ID NO 155
<211> LENGTH: 60
<212> TYPE: DNA
<213> ORGANISM: Homo sapiens

<400> SEQUENCE: 155
cttggttcat ctattttcat taaaccatag tctttgtctg ctggatgata cgtcgccaag    60

<210> SEQ ID NO 156
<211> LENGTH: 60
<212> TYPE: DNA
<213> ORGANISM: Homo sapiens

<400> SEQUENCE: 156
ccaaaacaga catgagccca ctgcttggaa caacaaactg tcctggttgc tggtcagagg    60

<210> SEQ ID NO 157
<211> LENGTH: 60
<212> TYPE: DNA
<213> ORGANISM: Homo sapiens

<400> SEQUENCE: 157
ggtcttggta gaagcgcgtg caaaagccat tctggacttc ctggatgccc tgctagagct    60

<210> SEQ ID NO 158
<211> LENGTH: 60
<212> TYPE: DNA
<213> ORGANISM: Homo sapiens

<400> SEQUENCE: 158
ggcagcagga agcggagtcg agaccacttc cggaacaaga gcagcagccc cgaggaccca    60

<210> SEQ ID NO 159
<211> LENGTH: 60
<212> TYPE: DNA
<213> ORGANISM: Homo sapiens

<400> SEQUENCE: 159
cggaagtcct gatgtatagc aagttcagca gcaaatctga catttgggct tttggggttt    60

<210> SEQ ID NO 160
<211> LENGTH: 60
<212> TYPE: DNA
<213> ORGANISM: Homo sapiens

<400> SEQUENCE: 160
agaacattgt accatgcctc ttctgtatct gtggaagttt cctgtttgac acagggtatc    60

<210> SEQ ID NO 161
<211> LENGTH: 60
<212> TYPE: DNA

<213> ORGANISM: Homo sapiens

<400> SEQUENCE: 161
tcagaaggct cttctgacta ctgggcaaag agtgtagatc agagcagcag tgaaaacaat    60

<210> SEQ ID NO 162
<211> LENGTH: 60
<212> TYPE: DNA
<213> ORGANISM: Homo sapiens

<400> SEQUENCE: 162
actaggaagt atatgccccc aaattatgaa attccatttc aaacagaatt aacagaattt    60

<210> SEQ ID NO 163
<211> LENGTH: 60
<212> TYPE: DNA
<213> ORGANISM: Homo sapiens

<400> SEQUENCE: 163
tttggggatt ttgttttccc ttggtctaat ggagagaaag acattttggt tttcttttc    60

<210> SEQ ID NO 164
<211> LENGTH: 60
<212> TYPE: DNA
<213> ORGANISM: Homo sapiens

<400> SEQUENCE: 164
ggtttattga catggaatga tttgaccaag gtgatatagt ggttaagcag ttaagtgatt    60

<210> SEQ ID NO 165
<211> LENGTH: 60
<212> TYPE: DNA
<213> ORGANISM: Homo sapiens

<400> SEQUENCE: 165
ctgagatgct gatgtcatgg agagtaaacg accacaagtt taccccactt ctctgtgaaa    60

<210> SEQ ID NO 166
<211> LENGTH: 60
<212> TYPE: DNA
<213> ORGANISM: Homo sapiens

<400> SEQUENCE: 166
tccagatgta aaccccaaac ttgtacacaa aagaaagcac agattgttta cctgttgtgg    60

<210> SEQ ID NO 167
<211> LENGTH: 60
<212> TYPE: DNA
<213> ORGANISM: Homo sapiens

<400> SEQUENCE: 167
ctttagacct ttgtccccgt cactgccagc gcttgggctg aaggaagctc cagactcaat    60

<210> SEQ ID NO 168
<211> LENGTH: 60
<212> TYPE: DNA
<213> ORGANISM: Homo sapiens

<400> SEQUENCE: 168
gggacatggg aggagccata ttgagaaagt agcatgggta cttggcttca cagagtgtgg    60

<210> SEQ ID NO 169
<211> LENGTH: 60

```
<212> TYPE: DNA
<213> ORGANISM: Homo sapiens

<400> SEQUENCE: 169
gctgattatt ggcatcatct ccattgtcct actcggttct taaaggcata tggacttgcc    60

<210> SEQ ID NO 170
<211> LENGTH: 60
<212> TYPE: DNA
<213> ORGANISM: Homo sapiens

<400> SEQUENCE: 170
aaggttccat ggtagctaag tgtggacaag ctaatcactg aagttccctg atgcagagtt    60

<210> SEQ ID NO 171
<211> LENGTH: 60
<212> TYPE: DNA
<213> ORGANISM: Homo sapiens

<400> SEQUENCE: 171
acagcccagc agggaggaag catcacacag cgttaggagc cgtttccttc aggtgttaag    60

<210> SEQ ID NO 172
<211> LENGTH: 60
<212> TYPE: DNA
<213> ORGANISM: Homo sapiens

<400> SEQUENCE: 172
agacattgag tcttttggga gacagaaggg agggagagtg ccagtcaaaa gggtttcgtg    60

<210> SEQ ID NO 173
<211> LENGTH: 60
<212> TYPE: DNA
<213> ORGANISM: Homo sapiens

<400> SEQUENCE: 173
atgagccgat gttgacaaga gcttaagtaa gtctccatgt acatcaagta ctttggagac    60

<210> SEQ ID NO 174
<211> LENGTH: 60
<212> TYPE: DNA
<213> ORGANISM: Homo sapiens

<400> SEQUENCE: 174
tgaaaaagtg caccacatgg atgttaagta gaaattcaag aaagtaagat gtcttcagca    60

<210> SEQ ID NO 175
<211> LENGTH: 60
<212> TYPE: DNA
<213> ORGANISM: Homo sapiens

<400> SEQUENCE: 175
gagacaaact caatgttaaa atctctagga gtgaccacga agtttcatag ttttccaaat    60

<210> SEQ ID NO 176
<211> LENGTH: 60
<212> TYPE: DNA
<213> ORGANISM: Homo sapiens

<400> SEQUENCE: 176
gatcagcacc tatgagttcg gcaaaagctt cttccagagg ctgaaccagg accggcttct    60

<210> SEQ ID NO 177
```

```
<211> LENGTH: 60
<212> TYPE: DNA
<213> ORGANISM: Homo sapiens

<400> SEQUENCE: 177
tttaaatctc cacagacgta tatggatggt ttactgcatt atgtatctgt aataagcgac    60

<210> SEQ ID NO 178
<211> LENGTH: 60
<212> TYPE: DNA
<213> ORGANISM: Homo sapiens

<400> SEQUENCE: 178
ggaaggcttc tgacgcttgt ggccagactg caattgcact tatgtgttat gctactaata    60

<210> SEQ ID NO 179
<211> LENGTH: 60
<212> TYPE: DNA
<213> ORGANISM: Homo sapiens

<400> SEQUENCE: 179
agaaaccagg aactatgtta aacaaagaaa agcttttggc aaaacagttg ctcacctaca    60

<210> SEQ ID NO 180
<211> LENGTH: 60
<212> TYPE: DNA
<213> ORGANISM: Homo sapiens

<400> SEQUENCE: 180
aaagatggtg gctgtgtctc tccccggtaa tgtcactgtt tttattcctt ccatctagca    60

<210> SEQ ID NO 181
<211> LENGTH: 60
<212> TYPE: DNA
<213> ORGANISM: Homo sapiens

<400> SEQUENCE: 181
ctataaggtt gtactgctgg gaaaatacaa tgcacagggc ttaggttcag atcatgaatt    60

<210> SEQ ID NO 182
<211> LENGTH: 60
<212> TYPE: DNA
<213> ORGANISM: Homo sapiens

<400> SEQUENCE: 182
tcaatgtaaa aactagaacc tttatatact ggggattata agattctact tactagaaat    60

<210> SEQ ID NO 183
<211> LENGTH: 60
<212> TYPE: DNA
<213> ORGANISM: Homo sapiens

<400> SEQUENCE: 183
gatcccttct caaactcaga accctagcag tgttacctta acaaaaatg agctcgagaa     60

<210> SEQ ID NO 184
<211> LENGTH: 60
<212> TYPE: DNA
<213> ORGANISM: Homo sapiens

<400> SEQUENCE: 184
aacgctgtcc gcatcatcca ggtctattgg cgctggagaa gttgccatac ccgtggcttt    60
```

<210> SEQ ID NO 185
<211> LENGTH: 60
<212> TYPE: DNA
<213> ORGANISM: Homo sapiens

<400> SEQUENCE: 185
tggggacagc caagttttgt tgataaacct atttcctagc atgccttcag gaagttgtgc    60

<210> SEQ ID NO 186
<211> LENGTH: 60
<212> TYPE: DNA
<213> ORGANISM: Homo sapiens

<400> SEQUENCE: 186
tcactcagga cttctctcct gaagaacacg cagtgctaaa actgaggatg atttccctaa    60

<210> SEQ ID NO 187
<211> LENGTH: 60
<212> TYPE: DNA
<213> ORGANISM: Homo sapiens

<400> SEQUENCE: 187
gaactgaaca ttgtttgtaa ggctgtggat gatggttaca atgtgcagcc agacaccgtg    60

<210> SEQ ID NO 188
<211> LENGTH: 60
<212> TYPE: DNA
<213> ORGANISM: Homo sapiens

<400> SEQUENCE: 188
ggtcttggta gaagcgcgtg caaaagccat tctggacttc ctggatgccc tgctagagct    60

<210> SEQ ID NO 189
<211> LENGTH: 60
<212> TYPE: DNA
<213> ORGANISM: Homo sapiens

<400> SEQUENCE: 189
gaaacaagtg ccatgaggcc ctcaagccaa actcttccaa ctgaataaat gagctaattc    60

<210> SEQ ID NO 190
<211> LENGTH: 60
<212> TYPE: DNA
<213> ORGANISM: Homo sapiens

<400> SEQUENCE: 190
tcaccctgca tatcctaggt ttgaagagaa acgctcagat ccgcttattt ctgccagtat    60

<210> SEQ ID NO 191
<211> LENGTH: 60
<212> TYPE: DNA
<213> ORGANISM: Homo sapiens

<400> SEQUENCE: 191
tgagccaagc acagtggtgg caaaagctta tttgtgtaca atcactggct tcatacttcc    60

<210> SEQ ID NO 192
<211> LENGTH: 60
<212> TYPE: DNA
<213> ORGANISM: Homo sapiens

<400> SEQUENCE: 192
tgtgtgcata gttactcagt ttttatgaac tgttgtatcc tgttaatgca tattgctctg    60

```
<210> SEQ ID NO 193
<211> LENGTH: 60
<212> TYPE: DNA
<213> ORGANISM: Homo sapiens

<400> SEQUENCE: 193
tggcacaccg tcaacaacac gatccctatg tccatgtgtt ccaagaggtg ccagtcaggg      60

<210> SEQ ID NO 194
<211> LENGTH: 60
<212> TYPE: DNA
<213> ORGANISM: Homo sapiens

<400> SEQUENCE: 194
tatgtacagt ttacatgaat gttcctcagg acatggcata caatggcctt ggaggtccaa      60

<210> SEQ ID NO 195
<211> LENGTH: 60
<212> TYPE: DNA
<213> ORGANISM: Homo sapiens

<400> SEQUENCE: 195
aaatagcatg tgacacagga cagccatagt atagtgtgtc actcgtggtt ggtgtccttt      60

<210> SEQ ID NO 196
<211> LENGTH: 60
<212> TYPE: DNA
<213> ORGANISM: Homo sapiens

<400> SEQUENCE: 196
agtgctggcc cagaacaggt ttctcctgga gctacagata agcaacaaca ggctggagga      60

<210> SEQ ID NO 197
<211> LENGTH: 60
<212> TYPE: DNA
<213> ORGANISM: Homo sapiens

<400> SEQUENCE: 197
tgtccttcat tcttttgatg tgatgtatcg catttacaga tctgaatatg tattaggtgg      60

<210> SEQ ID NO 198
<211> LENGTH: 60
<212> TYPE: DNA
<213> ORGANISM: Homo sapiens

<400> SEQUENCE: 198
tgactgtttt aatggggttt cacccaaatt gtttaatgct tctgctgtaa atgtcatact      60

<210> SEQ ID NO 199
<211> LENGTH: 60
<212> TYPE: DNA
<213> ORGANISM: Homo sapiens

<400> SEQUENCE: 199
tgactatgag accgttcgca atgggggcct gatcttcgct ggactggcct tcatcgtggg      60

<210> SEQ ID NO 200
<211> LENGTH: 60
<212> TYPE: DNA
<213> ORGANISM: Homo sapiens

<400> SEQUENCE: 200
aatcccatgg accctctgga ctacaaggat cagagtgcct ggaagtttca gatcttgtag      60
```

<210> SEQ ID NO 201
<211> LENGTH: 60
<212> TYPE: DNA
<213> ORGANISM: Homo sapiens

<400> SEQUENCE: 201
atgggtaata tcagcataat tgtattgatc agaagaagtc atcatcttca tacacccatg    60

<210> SEQ ID NO 202
<211> LENGTH: 60
<212> TYPE: DNA
<213> ORGANISM: Homo sapiens

<400> SEQUENCE: 202
tggaataatg ttctctgcta cttttaacct gattttcttt gtacctaaat aggcagctag    60

<210> SEQ ID NO 203
<211> LENGTH: 60
<212> TYPE: DNA
<213> ORGANISM: Homo sapiens

<400> SEQUENCE: 203
acaataagtt ctgcaaaacc ctctcattca tgaaaggtg ctccttgcta gacagaaact     60

<210> SEQ ID NO 204
<211> LENGTH: 60
<212> TYPE: DNA
<213> ORGANISM: Homo sapiens

<400> SEQUENCE: 204
acacgttttt ggaggatacc aagaagctgt accactcaga agcctcttcc atcaacttca    60

<210> SEQ ID NO 205
<211> LENGTH: 60
<212> TYPE: DNA
<213> ORGANISM: Homo sapiens

<400> SEQUENCE: 205
ggaaggcttc tgacgcttgt ggccagactg caattgcact tatgtgttat gctactaata    60

<210> SEQ ID NO 206
<211> LENGTH: 60
<212> TYPE: DNA
<213> ORGANISM: Homo sapiens

<400> SEQUENCE: 206
gctcttagaa cctcaggttc tcaggcaaga gccacctgct attgccgaac tggccgttgt    60

<210> SEQ ID NO 207
<211> LENGTH: 60
<212> TYPE: DNA
<213> ORGANISM: Homo sapiens

<400> SEQUENCE: 207
gcaggataag gacaaggcta cacaatggct tagaacagtt aatcgggcaa cagttggaaa    60

<210> SEQ ID NO 208
<211> LENGTH: 60
<212> TYPE: DNA
<213> ORGANISM: Homo sapiens

<400> SEQUENCE: 208

```
cgcataattc ggctcatctc cttagctgcc cagaaattca tctcagatat tgccaatgat        60

<210> SEQ ID NO 209
<211> LENGTH: 60
<212> TYPE: DNA
<213> ORGANISM: Homo sapiens

<400> SEQUENCE: 209
taacgtttcc ggtattactc tgctacacgt agccttttta cttttggggt tttgtttttg        60

<210> SEQ ID NO 210
<211> LENGTH: 26
<212> TYPE: DNA
<213> ORGANISM: Artificial Sequence
<220> FEATURE:
<223> OTHER INFORMATION: primer

<400> SEQUENCE: 210
tgatcaaact tatagatatt gcacga                                             26

<210> SEQ ID NO 211
<211> LENGTH: 23
<212> TYPE: DNA
<213> ORGANISM: Artificial Sequence
<220> FEATURE:
<223> OTHER INFORMATION: primer

<400> SEQUENCE: 211
tcatacagaa caattccaaa tgc                                                23
```